United States Patent [19]
Tsugita et al.

[11] Patent Number: 6,042,598
[45] Date of Patent: Mar. 28, 2000

[54] METHOD OF PROTECTING A PATIENT FROM EMBOLIZATION DURING CARDIAC SURGERY

[75] Inventors: Ross S. Tsugita, Mountain View; Tracy D. Maahs, Redwood City; Yue-Teh Jang, Fremont, all of Calif.

[73] Assignee: Embol-X Inc., Mountain View, Calif.

[21] Appl. No.: 09/286,195

[22] Filed: Apr. 5, 1999

Related U.S. Application Data

[62] Division of application No. 09/022,510, Feb. 12, 1998, Pat. No. 5,910,154, which is a continuation of application No. 08/852,867, May 8, 1997, Pat. No. 5,911,734.

[51] Int. Cl.$^7$ .................................................. A61M 29/00
[52] U.S. Cl. ........................................... 606/200; 128/898
[58] Field of Search .................................. 606/200, 191, 606/159, 198; 128/898

[56] References Cited

U.S. PATENT DOCUMENTS

| | | | |
|---|---|---|---|
| 4,580,568 | 4/1986 | Gianturco | 128/345 |
| 4,619,246 | 10/1986 | Molgaard-Nielsen et al. | 128/1 |
| 4,723,549 | 2/1988 | Wholey et al. | 128/344 |
| 4,733,665 | 3/1988 | Palmaz | 128/343 |
| 4,800,882 | 1/1989 | Gianturco | 128/343 |
| 4,873,978 | 10/1989 | Ginsburg | 128/345 |
| 4,907,336 | 3/1990 | Gianturco | 606/195 |
| 5,041,126 | 8/1991 | Gianturco | 606/195 |
| 5,053,008 | 10/1991 | Bajaj | 604/104 |
| 5,104,399 | 4/1992 | Lazarus | 623/1 |
| 5,108,419 | 4/1992 | Reger et al. | 606/200 |
| 5,152,777 | 10/1992 | Goldberg et al. | 606/200 |
| 5,160,342 | 11/1992 | Reger et al. | 606/200 |
| 5,306,286 | 4/1994 | Stack et al. | 606/198 |

(List continued on next page.)

FOREIGN PATENT DOCUMENTS

| | | |
|---|---|---|
| 0533511 | 3/1993 | European Pat. Off. . |
| 0686379 | 2/1995 | European Pat. Off. . |
| 0696447 | 10/1995 | European Pat. Off. . |
| WO96/01591 | 1/1996 | WIPO . |
| WO96/10375 | 4/1996 | WIPO . |
| WO96/23441 | 8/1996 | WIPO . |
| WO98/33443 | 8/1998 | WIPO . |
| WO99/22673 | 5/1999 | WIPO . |
| WO99/23976 | 5/1999 | WIPO . |

OTHER PUBLICATIONS

"Endovascular Grafts, Stents Drive Interventional Radiolovy Growth," *Cardiovascular Device Update*, 2(3):1–12 (Mar. 1996).

"Percutaneous Techniques for Endoluminal Carotid Interventions," *J. Endovasc. Surg.*, 3:182–202 (1996).

*Primary Examiner*—Michael Buiz
*Assistant Examiner*—Kevin Truong
*Attorney, Agent, or Firm*—Lyon & Lyon LLP

[57] ABSTRACT

An apparatus and method for treating stenosed blood vessels is provided, more particularly a percutaneous catheter, including a filter for capturing loose embolic material, used to deliver a stent, preferably within the ascending aorta, the aortic arch, or the carotid arteries. The catheter includes an expandable stent deployed on an inflatable balloon, or alternatively a self-expanding stent. A filter assembly is provided either directly on the catheter, or in a separate sheath or on a guidewire. The filter assembly comprises an expansion frame, having filter mesh attached to it, disposed on a guidewire inserted through the catheter or sheath, or alternatively attached directly on a distal region of the catheter. The expansion frame comprises a structure which is activated from a contracted condition into an enlarged condition in a blood vessel, thereby traversing the vessel with the filter mesh. The expansion frame includes biased struts, a mechanically operated frame, and/or a fluid-operated frame. The catheter is percutaneously introduced into a blood vessel and directed to a target region. The stent is localized across the region, the filter assembly is opened, and the stent is deployed, substantially permanently engaging the walls of the blood vessel, thereby opening the stenosed region and/or containing aortic plaque.

25 Claims, 17 Drawing Sheets

U.S. PATENT DOCUMENTS

| | | | |
|---|---|---|---|
| 5,314,444 | 5/1994 | Gianturco | 606/195 |
| 5,314,472 | 5/1994 | Fontaine | 623/12 |
| 5,330,500 | 7/1994 | Song | 606/198 |
| 5,350,398 | 9/1994 | Pavcnik et al. | 606/200 |
| 5,354,310 | 10/1994 | Garnic et al. | 606/198 |
| 5,356,423 | 10/1994 | Tihon et al. | 606/194 |
| 5,366,473 | 11/1994 | Winston et al. | 606/198 |
| 5,370,683 | 12/1994 | Fontaine | 623/1 |
| 5,383,892 | 1/1995 | Cardon et al. | 606/198 |
| 5,383,926 | 1/1995 | Locke et al. | 623/1 |
| 5,387,235 | 2/1995 | Chuter | 623/1 |
| 5,395,349 | 3/1995 | Quiachon et al. | 604/248 |
| 5,397,345 | 3/1995 | Lazarus | 623/1 |
| 5,405,377 | 4/1995 | Cragg | 623/1 |
| 5,423,885 | 6/1995 | Williams | 623/1 |
| 5,425,765 | 6/1995 | Tiefenbrun et al. | 623/12 |
| 5,443,498 | 8/1995 | Fontaine | 623/1 |
| 5,449,372 | 9/1995 | Schmaltz et al. | 606/198 |
| 5,484,418 | 1/1996 | Quiachon et al. | 604/167 |
| 5,507,767 | 4/1996 | Maeda et al. | 606/198 |
| 5,527,354 | 6/1996 | Fontaine et al. | 623/1 |
| 5,569,274 | 10/1996 | Rapacki et al. | 606/158 |
| 5,569,275 | 10/1996 | Kotula et al. | 606/159 |
| 5,695,519 | 12/1997 | Summers et al. | 606/200 |
| 5,814,064 | 9/1998 | Daniel et al. | 606/200 |
| 5,827,324 | 10/1998 | Cassell et al. | 606/200 |
| 5,925,062 | 7/1999 | Purdy | 606/200 |
| 5,928,260 | 7/1999 | Chin et al. | 606/200 |

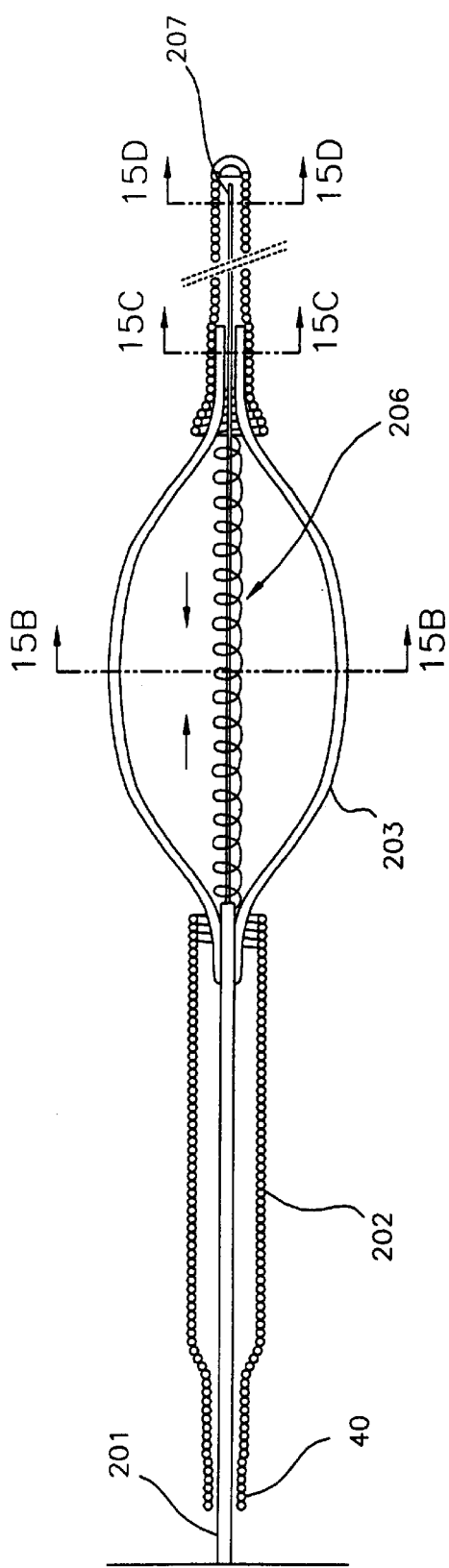
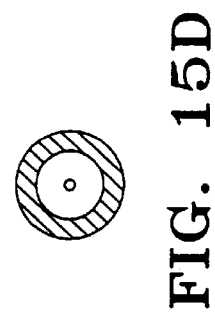
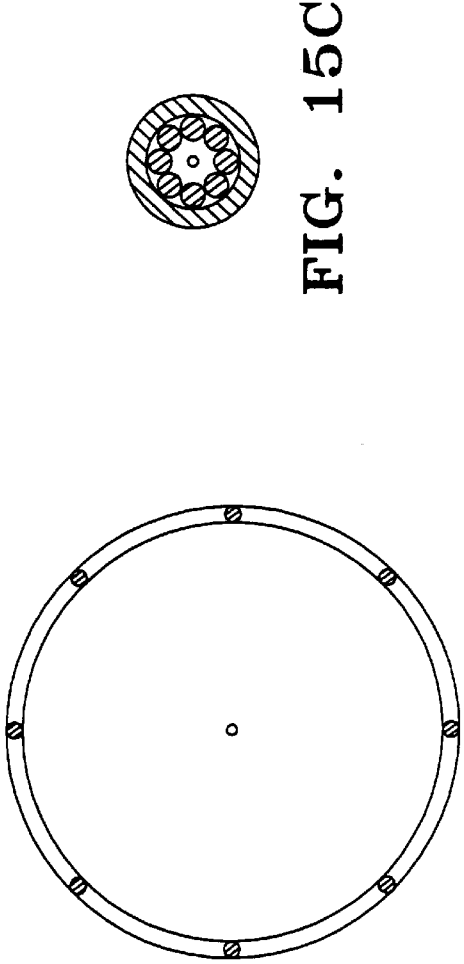
FIG. 15A
FIG. 15D
FIG. 15C
FIG. 15B

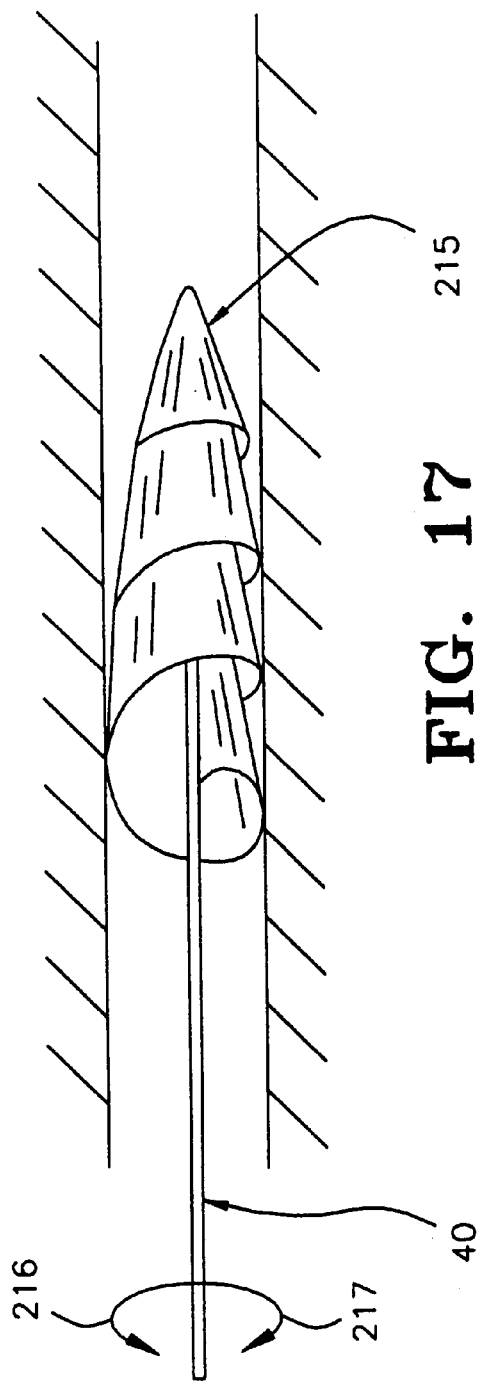
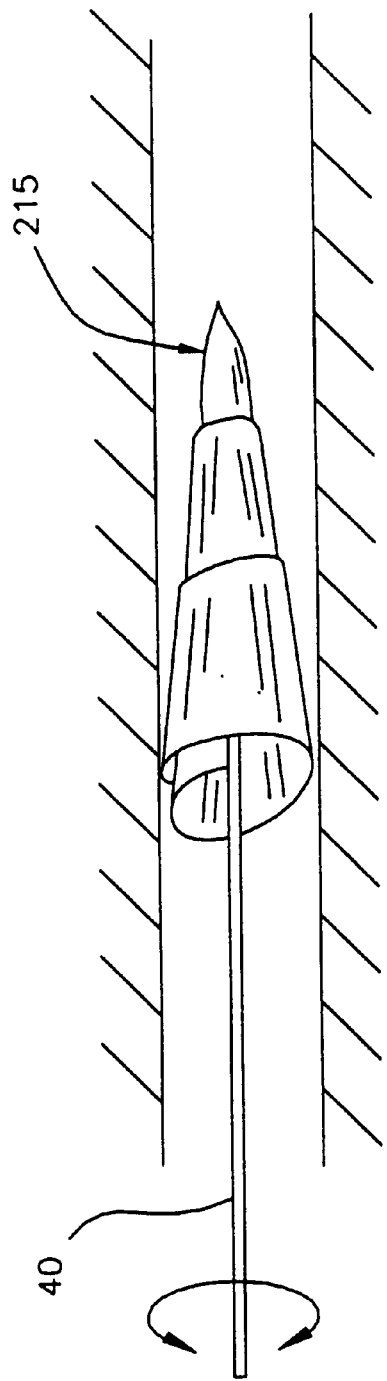

METHOD OF PROTECTING A PATIENT FROM EMBOLIZATION DURING CARDIAC SURGERY

This is a division of application Ser. No. 09/022,510, filed Feb. 12, 1998 now U.S. Pat. No. 5,910,154, which is a continuation of application Ser. No. 08/852,867, filed May 8, 1997 now U.S. Pat. No. 5,911,734. Both of the above applications are hereby and fully incorporated herein by reference.

FIELD OF THE INVENTION

The present invention relates generally to treating plaque deposits and occlusions within major blood vessels, more particularly to an apparatus and method for preventing detachment of mobile aortic plaque within the ascending aorta, the aortic arch, or the carotid arteries, and to an apparatus and method for providing a stent and a filter in a percutaneous catheter for treating occlusions within the carotid arteries.

BACKGROUND

Several procedures are now used to open stenosed or occluded blood vessels in a patient caused by the deposit of plaque or other material on the walls of the blood vessels. Angioplasty, for example, is a widely known procedure wherein an inflatable balloon is introduced into the occluded region. The balloon is inflated, dilating the occlusion, and thereby increasing intraluminal diameter. Plaque material may be inadvertently dislodged during angioplasty, and this material is then free to travel downstream, possibly lodging within another portion of the blood vessel or possibly reaching a vital organ, causing damage to the patient.

In another procedure, stenosis within arteries and other blood vessels is treated by permanently or temporarily introducing a stent into the stenosed region to open the lumen of the vessel. The stent typically comprises a substantially cylindrical tube or mesh sleeve made from such materials as stainless steel or nitinol. The design of the material permits the diameter of the stent to be radially expanded, while still providing sufficient rigidity such that the stent maintains its shape once it has been enlarged to a desired size.

Generally, a stent having a length longer than the target region is selected and is disposed on a catheter prior to use. The catheter typically has a flexible balloon, near its distal end, designed to inflate to a desired size when subjected to internal pressure. The stent is mounted to the catheter and compressed over the balloon, typically by hand, to assure that the stent does not move as it passes through the blood vessel to the desired location within the patient. Alternatively, self-expanding stents may also be used.

The stent is typically introduced into the desired blood vessel using known percutaneous methods. The catheter, having the stent securely crimped thereon, is directed to the region of the blood vessel being treated. The catheter is positioned such that the stent is centered across the stenosed region. The balloon is inflated, typically by introducing gas or fluid such as saline solution, through a lumen in the catheter communicating with the balloon. Balloon inflation causes the stent to expand radially, thereby engaging the stenosed material. As the stent expands, the material is forced outward, dilating the lumen of the blood vessel.

Due to substantial rigidity of the stent material, the stent retains its expanded shape, providing an open passage for blood flow. The balloon is then deflated and the catheter withdrawn.

Because the stent is often constructed from a mesh material, the stent typically compresses longitudinally as it expands radially. Stenotic material trapped between the stent and the vessel wall may extend into the openings in the mesh and may be sheared off by this longitudinal compression to create embolic debris free. When this material travels downstream, it can cause serious complications. For example loose embolic material released within the ascending aorta, the aortic arch, or the carotid arteries may travel downstream to the brain, possibly causing stroke, which can lead to permanent injuries or even death of the patient.

Thus, there is a need for an apparatus and method for delivering a stent into an arterial occlusion which substantially reduces the risk of embolic material escaping to the vessel and causing a blockage at a downstream location. There is also an apparatus and method for substantially preventing detachment of plaque deposited on the walls of the ascending aorta, the aortic arch, the descending aorta, and the carotid arteries. In addition, there is a need for an apparatus and method to substantially contain loose embolic material within the aorta and the carotid arteries during an interventional procedure, preventing it from reaching the brain.

SUMMARY OF THE INVENTION

The present invention provides an apparatus and method for preventing embolic material from escaping a site of intervention within the aorta, the carotid arteries, and other arteries generally, thereafter causing damage to vital organs, such as the brain. More particularly, the present invention involves an apparatus and method for introducing a stent into a region of a major blood vessel within the human body having plaque deposits, such as the ascending aorta, the descending aorta, aortic arch, common carotid artery, external and internal carotid arteries, brachiocephalic trunk, middle cerebral artery, anterior cerebral artery, posterior cerebral artery, vertebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, and posterior tibial artery, thereby opening occlusions and/or preventing embolic material from breaking free within the blood vessel.

In a first embodiment, the invention includes a guidewire having an expandable filter attached to it, and a stent catheter. The catheter has an inflatable balloon mounted on or near its distal end, and an inflation lumen extending through the catheter between a proximal region of the catheter and the balloon. A stent is provided on the outer surface of the catheter, substantially engaging the balloon. Generally, the stent comprises an expandable substantially rigid tube, sheet, wire or spring, but preferably a cylindrical mesh sleeve. See Palmaz, U.S. Pat. No. 4,733,665, incorporated herein by reference.

Alternatively, the stent may be a self-expanding sleeve, preferably from nitinol. In this case, the stent catheter does not require an inflatable balloon. Instead the stent is compressed over the catheter and a sheath or outer catheter is directed over the stent to hold it in the compressed condition until time of deployment.

The guidewire has a filter assembly attached at or near its distal end, which includes an expansion frame which is adapted to open from a contracted condition to an enlarged condition. Filter material, typically a fine mesh, is attached to the expansion frame to filter undesirable embolic material from blood.

The guidewire with the expansion frame in its contracted condition is provided through a sheath or cannula, or preferably is included directly in the stent catheter. The catheter typically has a second lumen extending from its proximal region to its distal end into which the guidewire is introduced. The filter assembly on the distal end of the guidewire is then available to be extended beyond the distal end of the catheter for use during stent delivery.

The device is typically used to introduce a stent into a stenosed or occluded region of a patient, preferably within the carotid arteries. The catheter is introduced percutaneously into a blood vessel and is directed through the blood vessel to the desired region. If the filter device is provided in a separate sheath, the sheath is percutaneously inserted into the blood vessel downstream of the region being treated, and is fixed in position.

The filter assembly is introduced into the blood vessel, and the expansion frame is opened to its enlarged condition, extending the filter mesh substantially across the blood vessel until the filter mesh substantially engages the walls of the vessel.

The catheter is inserted through the region being treated until the stent is centered across the plaque deposited on the walls of the blood vessel. Fluid, preferably saline solution, is introduced through the inflation lumen, inflating the balloon, and expanding the stent radially outwardly to engage the plaque. The stent pushes the plaque away from the region, dilating the vessel. The balloon is deflated, and the catheter is withdrawn from the region and out of the patient. The stent remains substantially permanently in place, opening the vessel and trapping the plaque beneath the stent.

When the stenosed region is opened, embolic material may break loose from the wall of the vessel, but will encounter the filter mesh and be captured therein, rather than traveling on to lodge itself elsewhere in the body. After the stent is delivered, the expansion frame is closed, containing any material captured in the filter mesh. The filter assembly is withdrawn back into the sheath or the catheter itself, which is then removed from the body.

If a self-expanding stent is used, the stent catheter with the compressed stent thereon is inserted into a sheath, which restrains the stent in a compressed condition. The catheter is introduced into the patient's blood vessel and directed to the target region. Once the stent is localized across the stenosed region and the filter assembly is in position, the sheath is drawn proximally in relation to the catheter. This exposes the stent, which expands to engage the wall of the blood vessel, opening the lumen. The filter assembly is then closed and the catheter withdrawn from the patient.

The filter assembly has a number of preferred forms. For example, the expansion frame may comprise a plurality of struts or arms attached to and extending distally from the distal end of the guidewire. The struts are connected to each other at each end and have an intermediate region which is biased to expand radially. Filter mesh is attached typically between the intermediate region and the distal ends of the struts, thereby defining a substantially hemispherical or conical shaped filter assembly.

To allow the filter assembly to be inserted into the lumen of the sheath, the intermediate region of the expansion frame is compressed. When the filter assembly is ready to be introduced into a blood vessel, the guidewire is pushed distally. The expansion frame exits the lumen, and the struts automatically open radially. This expands the filter mesh to substantially traverse the vessel. After the stent is delivered, the guidewire is pulled proximally to withdraw the filter assembly. The struts contact the wall of the filter lumen, forcing them to compress, closing the frame as the filter assembly is pulled into the sheath.

In another embodiment, the expansion frame includes a plurality of struts attached to the distal end of the sheath. The struts extend distally from the sheath and attach to the distal end of the guidewire which is exposed beyond the sheath. At an intermediate region, the struts are notched or otherwise biased to fold out radially. Filter mesh is attached to the struts between the intermediate region and the distal end of the guidewire.

The filter assembly is directed into position in the blood vessel, either exposed on the end of the sheath or preferably within a second sheath which is withdrawn partially to expose the filter assembly. With the sheath fixed, the guidewire is pulled proximally. This compresses the struts, causing them to bend or buckle at the intermediate region and move radially outwardly, expanding the filter mesh across the blood vessel. After use, the guidewire is pushed distally, pulling the struts back down and closing the filter mesh.

In an alternative to this embodiment, the struts attached to the distal end of the sheath and to the distal end of the guidewire are biased to expand radially at an intermediate region. The filter mesh is attached to the struts between the intermediate region and the distal end of the guidewire. Prior to introduction into a patient, the guidewire is rotated torsionally in relation to the sheath, twisting the struts axially around the guidewire and compressing the filter mesh. Once in position in the blood vessel, the guidewire is rotated in the opposite direction, unwinding the struts. The struts expand radially, opening the filter mesh. After use, the guidewire is rotated once again, twisting the struts and closing the filter mesh for removal.

In yet another embodiment, the filter assembly comprises a plurality of substantially cylindrical compressible sponge-like devices attached in series to the guidewire. The devices have an uncompressed diameter substantially the same as the open regions of the blood vessel. They are sufficiently porous to allow blood to pass freely through them but to entrap undesirable substantially larger particles, such as loose embolic material.

The devices are compressed into the lumen of the sheath prior to use. Once in position, they are introduced into the blood vessel by pushing the guidewire distally. The devices enter the vessel and expand to their uncompressed size, substantially engaging the walls of the blood vessel. After use, the guidewire is pulled proximally, forcing the devices against the distal end of the sheath and compressing them back into the lumen.

In a second embodiment, a stent catheter and filter assembly are also provided. Unlike the previous embodiments, the filter assembly is not primarily mechanically operated, but is instead, generally fluid operated. Typically, the stent catheter includes a second balloon on or near the distal end of the catheter. A second inflation lumen extends through the catheter from the proximal region of the catheter to the balloon. The balloon is part of the expansion frame or alternatively merely activates the expansion frame, opening the filter assembly to the enlarged condition for use and closing it after being used.

In one form, the balloon has an annular shape. Filter mesh is attached around the perimeter of the balloon, creating a conical or hemispherical-shaped filter assembly. A flexible lumen extends between the balloon and the inflation lumen within the catheter. Optionally, retaining wires are connected symmetrically between the balloon and the catheter, thereby holding the balloon substantially in a desired relationship to the catheter.

When deflated, the balloon substantially engages the periphery of the catheter, holding the filter mesh closed and allowing the catheter to be directed to the desired location. Once the catheter is in position, the balloon is inflated. The balloon expands radially until it engages the walls of the blood vessel, the filter mesh thereby substantially traversing the vessel. After use, the balloon is deflated until it once again engages the perimeter of the catheter, thereby trapping any embolic material between the filter mesh and the outer wall of the catheter.

Alternatively, the balloon of this embodiment may be provided on the catheter proximal of the stent for retrograde use. In this case, the filter mesh is extended between the balloon and the outer surface of the catheter, instead of having a closed end.

In a third embodiment of the present invention, a method is provided in which a stent catheter is used to prevent the detachment of mobile aortic deposits within the ascending aorta, the aortic arch or the carotid arteries, either with or without an expandable filter assembly. A stent catheter, as previously described, is provided having an inflatable balloon and a stent thereon, or alternatively a self-expanding stent and a retaining sheath. The catheter is percutaneously introduced into a blood vessel and is directed to a region having mobile aortic plaque deposits, preferably a portion of the ascending aorta or the aortic arch.

The stent is positioned across the desired region, and the balloon is inflated. This expands the stent to engage the plaque deposits and the walls of the blood vessel, thereby trapping the plaque deposits. The balloon is deflated, and the catheter is removed from the blood vessel. Alternatively if a self-expanding stent is used, the sheath is partially withdrawn proximally, and the stent is exposed, allowing it to expand. The stent substantially retains its expanded configuration, thereby containing the plaque beneath the stent and preventing the plaque from subsequently detaching from the region and traveling downstream.

Optionally, a filter device similar to those already described may be introduced at a location downstream of the treated region. The filter device may be provided in a sheath which is inserted percutaneously into the blood vessel. Preferably, however, a filter device is attached to the stent catheter at a location proximal to the stent. Instead of attaching the filter assembly to a guidewire, it is connected directly to the outer surface of the catheter proximal to the stent. A sheath or cannula is typically provided over the catheter to cover the filter assembly.

Once the catheter is in position within the vessel, the sheath is withdrawn proximally, the filter assembly is exposed and is expanded to its enlarged condition. In a preferred form, the expansion frame includes biased struts similar to the those described above, such that when the filter assembly is exposed, the struts automatically expand radially, and filter mesh attached to the struts is opened. After the stent is deployed, the sheath is moved proximally, covering the expansion frame and compressing the struts back into the contracted condition. The catheter and sheath are then withdrawn from the patient.

Thus, an object of the present invention is to provide an apparatus and method for substantially preventing mobile aortic plaque deposited within the ascending aorta, the aortic arch, or the carotid arteries from detaching and traveling to undesired regions of the body.

Another object is to provide an apparatus and method for treating stenosed or occluded regions within the carotid arteries.

An additional object is to provide an apparatus and method for introducing a stent to treat a stenosed or occluded region of the carotid arteries which substantially captures any embolic material released during the procedure.

BRIEF DESCRIPTION OF THE DRAWINGS

For a better understanding of the invention, and to show how it may be carried into effect, reference will be made, by way of example, to the accompanying drawings, in which:

FIGS. 15 and 15A show detailed longitudinal views of a guidewire filter in accordance with the present invention.

FIGS. 17 and 17A show longitudinal views of a filter scroll in accordance with the present invention.

DESCRIPTION OF THE PREFERRED EMBODIMENTS

Figure 1:
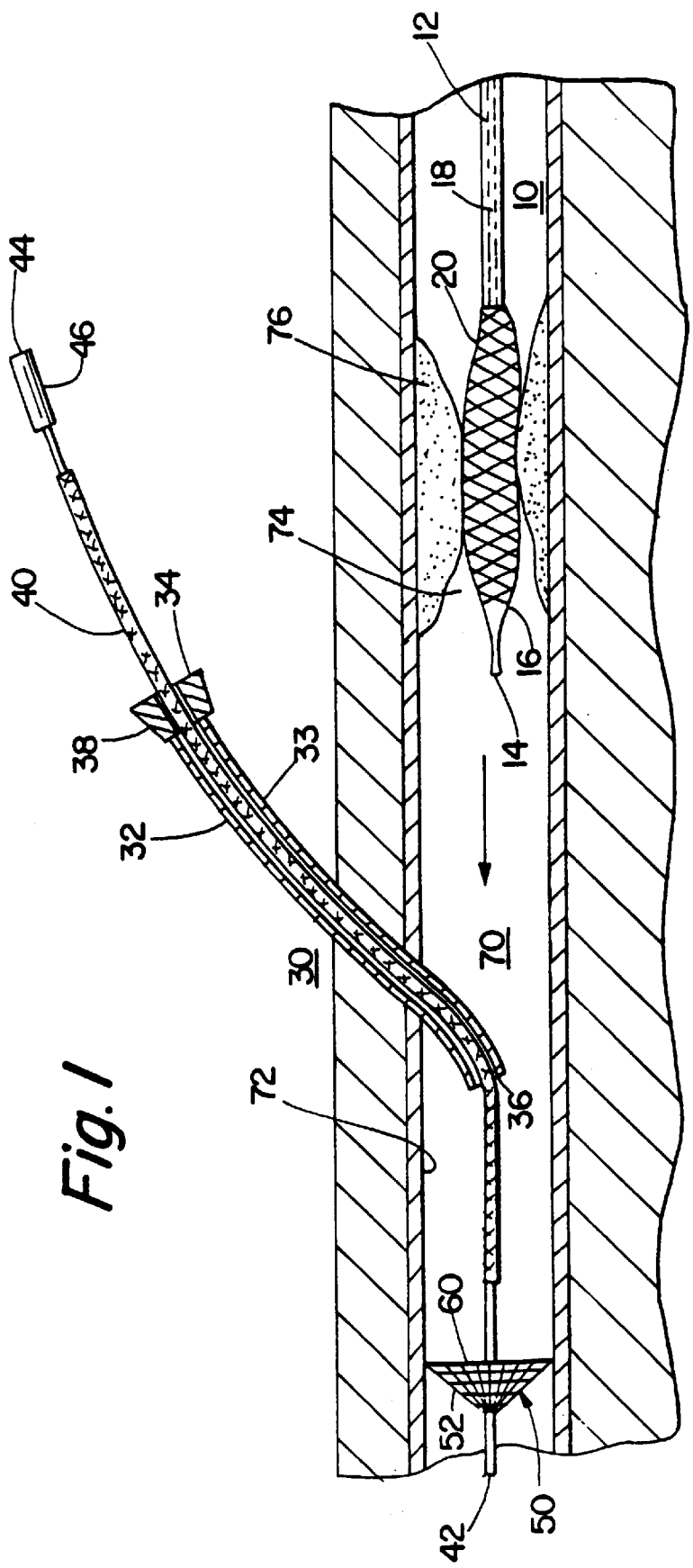
FIG. 1 is a longitudinal view of an embodiment being inserted into a blood vessel, namely a stent catheter in a stenosed region and a filter device downstream of the region.

Turning to FIG. 1, a first embodiment of the present invention is shown, namely a stent catheter 10 and a filter device 30. The stent catheter 10 typically includes a catheter body 12, an inflatable balloon 16, and a stent 20. The catheter body 12 typically comprises a substantially flexible member having a proximal end (not shown) and a distal end 14. The balloon is mounted on a region at or near the distal end 14 of the catheter body 12. An inflation lumen 18 extends longitudinally from a region at or near the proximal end of the catheter body 12 to the balloon 16.

The stent 20 is introduced over the balloon 16, typically by manually compressing it onto the balloon 16. The stent 20 may comprise a tube, sheet, wire, mesh or spring, although preferably, it is a substantially cylindrical wire mesh sleeve, that is substantially rigid, yet expandable when subjected to radial pressure. Many known stent devices are appropriate for use with the present invention, such as those discussed elsewhere in this disclosure. Generally the stent is furnished from materials such as stainless steel or nitinol, with stainless steel being most preferred.

Alternatively, a self-expanding stent (not shown) may also be used, such as those disclosed in Regan, U.S. Pat. No. 4,795,458, Harada et al., U.S. Pat. No. 5,037,427, Harada, U.S. Pat. No. 5,089,005, and Mori, U.S. Pat. No. 5,466,242, the disclosures of which are incorporated herein by reference. Such stents are typically provided from nitinol or similar materials which are substantially resilient, yet compressible. When an expandable stent is used, the stent catheter does not generally include an inflatable balloon for the stent. Instead, the stent is compressed directly onto the catheter, and a sheath is placed over the stent to prevent it from expanding until deployed.

In addition to the catheter 10, the present invention typically includes a filter device 30. The filter device 30 generally comprises an introducer sheath 32, a guidewire 40, and an expandable filter assembly 50, although alternatively the guidewire 40 and the filter assembly 50 may be provided directly on the catheter 10 as will be described below (see FIG. 2). The sheath 32 has a proximal end 34 and a distal end 36, and generally includes a hemostatic seal 38 mounted on its proximal end 34. The guidewire 40, typically a flexible, substantially resilient wire, having a distal end 42 and a proximal end 44, is inserted into the proximal end 34 of the sheath 32 through a lumen 33. A hub or handle 46 is generally mounted on the proximal end 44 for controlling the guidewire 40.

Generally, attached on or near the distal end 42 of the guidewire 40 is an expandable filter assembly 50 which generally comprises an expansion frame 52 and filter mesh 60. The expansion frame 52 is generally adapted to open from a contracted condition while it is introduced through the lumen 33 of the sheath 32 to an enlarged condition once it is exposed within a blood vessel 70, as will be discussed more particularly below. The filter mesh 60 is substantially permanently attached to the expansion frame 52.

The construction of the stent catheter 10 should already be familiar to those skilled in the art. The catheter body 12 is typically made from substantially flexible materials such as polyethylene, nylon, PVC, polyurethane, or silicone, although materials such as polyethylene and PVC are preferred. The balloon 16 for delivering the stent 20 is generally manufactured from a substantially flexible and resilient material, such as polyethylene, polyester, latex, silicone, or more preferably polyethylene and polyester. A variety of balloons for angioplasty or stenting procedures are available which have a range of known inflated lengths and diameters, allowing an appropriate balloon to be chosen specifically for the particular blood vessel being treated.

The sheath 32 for the filter device 30 generally comprises a conventional flexible sheath or cannula for introducing catheters or guidewires into the blood stream of a patient. Exemplary materials include polyethylene, nylon, PVC, or polyurethane with polyethylene and pvc being most preferred. The hemostatic seal 38 generally is an annular seal designed to prevent the escape of blood from the vessel through the sheath 32, and includes materials such as silicone, latex, or urethane, or more preferably silicone. The hemostatic seal 38 is substantially permanently adhered to the proximal end 34 of the sheath 32 using known surgically safe bonding materials.

The guidewire 40 is generally manufactured from conventional resilient wire such as stainless steel or nitinol, although stainless steel is preferred, having a conventional hub or handle 46 formed integral with attached to its proximal end 44.

Figure 3:
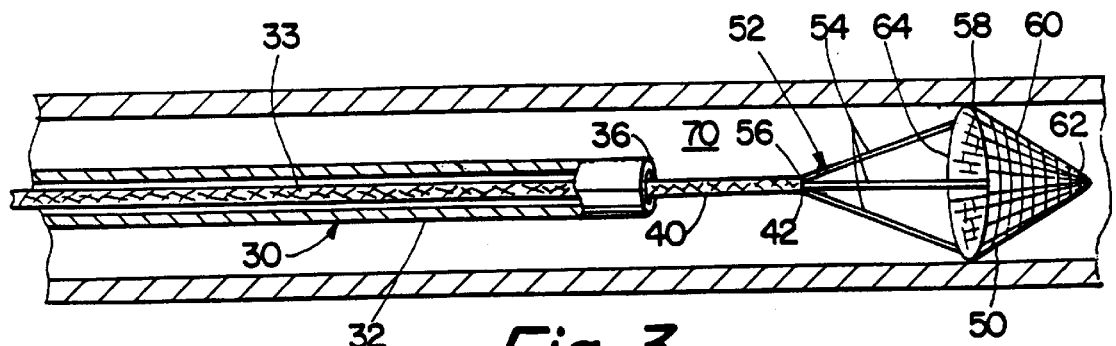
FIG. 3 is a longitudinal view of an embodiment of the filter assembly in its enlarged condition within a blood vessel.

Turning now to FIG. 3, the filter assembly 50 of the present invention is generally shown extending from the distal end 36 of a sheath or catheter 32 and in an enlarged condition within a blood vessel 70. The filter assembly 50 includes an expansion frame 52 comprising a plurality of struts, ribs or wires 54, each strut 54 having a substantially fixed proximal end 56 and a distal end 58, which may or may not be fixed. The proximal ends 56 are typically connected to the distal end 42 of the guidewire 40, or alternatively to the outer surface of a distal region (not shown in FIG. 3) of the guidewire 40, typically using conventional bonding methods, such as welding, soldering, or gluing. The distal ends 58 of the struts 54 are connected to the filter mesh 60, or alternatively to the distal end of the guidewire (not shown). The struts generally comprise substantially resilient materials such as stainless steel or nitinol, with stainless steel being preferred.

Generally, the filter mesh 60 comprises a fine mesh having an open region 64 substantially engaging the wall 72 of the blood vessel 70 and a closed region 62, shown here as the apex of a cone. An appropriate mesh is selected, having a pore size that permits blood to flow freely through the mesh, while capturing therein undesired particles of a targeted size. Appropriate filter materials are disclosed in co-pending applications Barbut et al., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30, 1996, Barbut et al., U.S. application Ser. No. 08/645,762, filed May 14, 1996, and Maahs, U.S. application Ser. No. [Lyon & Lyon attorney docket no. 224/194], filed Apr. 16, 1997. The disclosure of these references and any others cited herein are expressly incorporated herein by reference. An exemplary embodiment of the mesh has a mesh area of 3–8 sq. in., a mesh thickness of 60–200 µm, a thread diameter of 30–100 µm, and a pore size of 60–100 µm. Polyethylene meshes, such as Saati Tech and Tetko, Inc. meshes, provide acceptable filter materials, as they are available in sheet form and can be easily cut and formed into a desired shape. The mesh is formed into a desired filter shape and is sonic welded or adhesive bonded to the struts 54.

Figure 14:
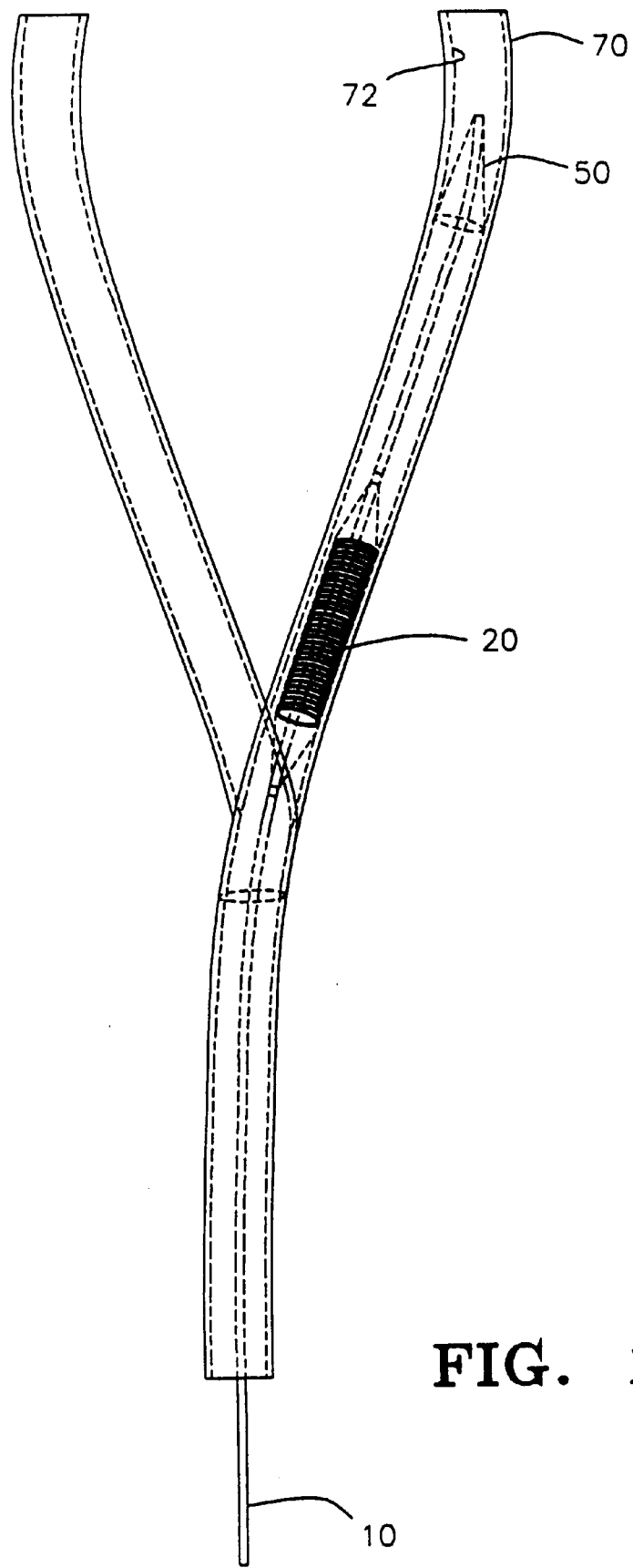
FIG. 14 depicts a longitudinal view of a stent deployment device having a distal filter disposed within a carotid artery.

The present invention is then typically used to introduce a stent into a stenosed or occluded region of a patient, preferably for treating a region within the carotid arteries. Referring again to FIGS. 1 and 2, the catheter 10 is first introduced into a blood vessel 70 using known percutaneous procedures, and then is directed through the blood vessel to the stenosed region of the target blood vessel. The catheter 10 is typically introduced in an upstream-to-downstream (antegrade) orientation as shown in FIGS. 1 and 14, although the catheter may also be introduced in a downstream-to-upstream (retrograde) orientation as will be described below. In a preferred example, the catheter 10 is inserted into a femoral artery and directed using known methods to a carotid artery, as shown in FIG. 14, or alternatively is introduced through a lower region of a carotid artery and directed downstream to the stenosed location 74.

The sheath 32 is percutaneously introduced into the blood vessel 70 downstream of the stenosed region 74, and is deployed using conventional methods. The distal end 42 of the guidewire 40 is directed through the lumen 33 of the sheath 32 until the filter assembly 50 is introduced into the blood vessel 70 by pushing distally on the hub 46 on the guidewire 40. When the distal end 42 of the guidewire 40 enters the blood vessel 70, the expansion frame 52 is opened to its enlarged condition, extending substantially across the entire cross-section of the vessel 70. The filter mesh 60 attached to the frame 52 substantially engages the luminal walls 72 of the vessel 70, thereby capturing any undesirable loose material passing along the blood vessel 70 from the treated region 74.

The catheter 10 is inserted through the stenosed region 74 until the stent 20 is centered across the plaque or embolic material 76 deposited on the walls 72 of the blood vessel 70. If the region 74 is substantially blocked, it may be necessary to first open the region 74 using a balloon catheter prior to insertion of the stent catheter (not shown in FIG. 3), as will be familiar to those skilled in the art. Once the stent 20 is in the desired position, fluid, saline, or radiographic contrast media, but preferably radiographic contrast media, is introduced through the inflation lumen 18 to inflate the balloon 16. As the balloon 16 expands, the pressure forces the stent 20 radially outwardly to engage the plaque 76. The plaque 76 is pushed away from the region 74, opening the vessel 70. The stent 20 covers the plaque 76, substantially permanently trapping it between the stent 20 and the wall 72 of the vessel 70. Once the balloon 16 is fully inflated, the stent 20 provides a cross-section similar to the clear region of the vessel 70. The balloon 16 is then deflated by withdrawing the fluid out of the inflation lumen 18 and the catheter 12 is withdrawn from the region 74 and out of the patient using conventional methods. The stent 20 remains in place, substantially permanently covering the plaque 76 in the treated region 74 and forming part of the lumen of the vessel 70.

As the stenosed region 74 is being opened, or possibly as the catheter 12 is being introduced through the region 74, plaque may break loose from the wall 72 of the vessel 70. Blood flow will carry the material downstream where it will encounter the filter mesh 60 and be captured therein. Once the catheter 12 is removed from the treated region 74, the expansion frame 52 for the filter mesh 60 is closed to the contracted position, containing any material captured therein. The filter assembly 50 is withdrawn into the lumen 33 of the sheath 32, and the filter device 30 is removed from the body.

Figure 2:
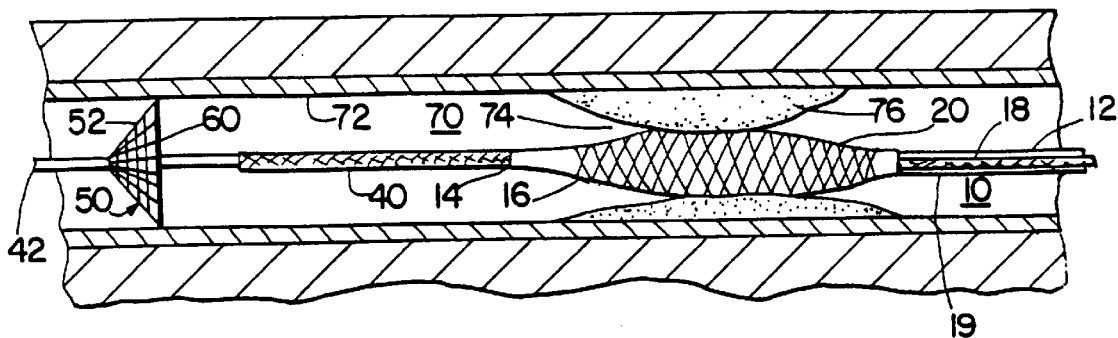
FIG. 2 is a longitudinal view of another embodiment, showing the filter device included in the stent catheter.

In another embodiment, shown in FIG. 2, the guidewire 40 and the filter assembly 50 are included within the stent catheter 10, rather than being provided in a separate sheath, thus eliminating the need for a second percutaneous puncture into the patient. As already described, the catheter 12 is provided with an inflatable balloon 16 furnished near its distal end 14 and with a stent 20 compressed over the balloon 16. In addition to the inflation lumen 18, a second lumen 19 extends through the catheter 12 from a proximal region (not shown) to its distal end 14. A guidewire 40, having a filter assembly 50 on its distal end 42, is introduced through the lumen 19 until its distal end 42 reaches the distal end 14 of the catheter 12. As before, the filter assembly 50 comprises an expansion frame 52 and filter mesh 60, which remain within the lumen 19 of the catheter 12 until deployed.

As described above, the stent catheter 10 is percutaneously introduced and is directed through the blood vessels until it reaches the stenosed region 74 and the stent 20 is centered across the plaque 76. The guidewire 40 is pushed distally, introducing the filter assembly 50 into the blood vessel 70. The expansion frame 52 is opened to the enlarged condition until the filter mesh 60 engages the walls 72 of the blood vessel 70. The balloon 16 is then inflated, pushing the stent 20 against the plaque 76, opening the treated region 74. As before, the stent 20 substantially permanently engages the plaque 76 and becomes part of the lumen 72 of the vessel 70. After the balloon 16 is deflated, the expansion frame 52 of the filter assembly 50 is closed to the contracted condition, and the filter assembly 50 is withdrawn into the lumen 19. The stent catheter 10 is then withdrawn from the patient using conventional procedures.

Alternatively, a self-expanding stent may be substituted for the expandable stent described above. Generally, the stent is compressed onto a catheter, and a sheath is introduced over the catheter and stent. The sheath serves to retain the stent in its compressed form until time of deployment. The catheter is percutaneously introduced into a patient and directed to the target location within the vessel. With the stent in position, the catheter is fixed and the sheath is withdrawn proximally. Once exposed within the blood vessel, the stent automatically expands radially, until it substantially engages the walls of the blood vessel, thereby trapping the embolic material and dilating the vessel. The catheter and sheath are then removed from the patient.

The filter assembly 50 generally described above has a number of possible configurations. Hereinafter reference is generally made to the filter device described above having a separate sheath, although the same filter assemblies may be incorporated directly into the stent catheter.

Figure 4A:
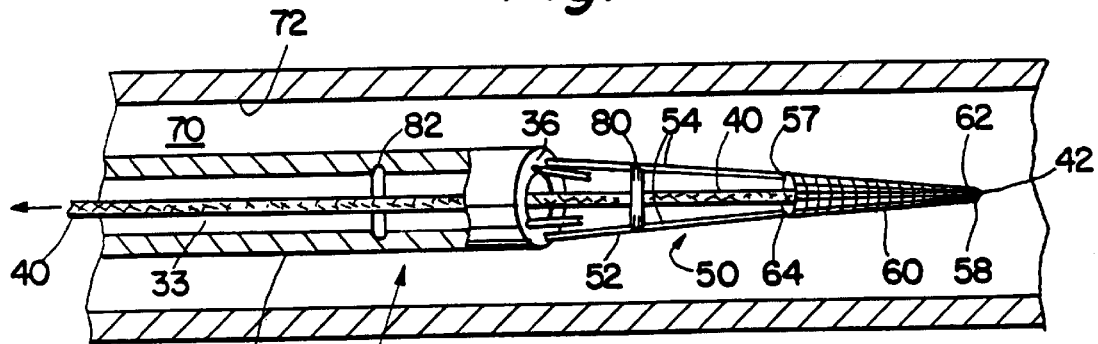
FIGS. 4A, 4B and 4C show a longitudinal view of an embodiment of the filter assembly in a contracted condition, a partially expanded condition, and an enlarged condition respectively within a blood vessel.
Figures 4B, 4C:
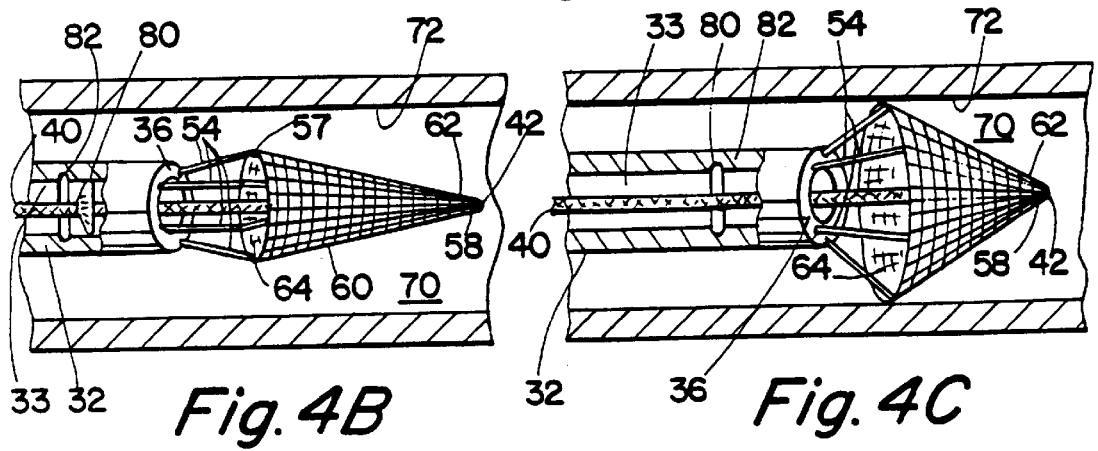

Turning to FIGS. 4A, 4B, and 4C, another embodiment of the filter device 30 is shown, namely a sheath 32 having a guidewire 40 in its lumen 33 and a filter assembly 50 extending from the distal end 36 of sheath 32. The filter assembly 50 comprises a plurality of struts 54 and filter mesh 60. The guidewire 40 continues distally through the filter mesh 60 to the closed end region 62. The proximal ends 56 of the struts 54 are attached to the distal end 36 of the sheath 32, while the distal ends 58 of the struts 54 are attached to the distal end 42 of the guidewire. In FIG. 4A, showing the contracted condition, the struts 54 are substantially straight and extend distally. At an intermediate region 57, the open end 64 of the filter mesh 60 is attached to the struts 54 using the methods previously described. The filter mesh 60 may be attached to the struts 54 only at the intermediate region 57 or preferably continuously from the intermediate region 57 to the distal ends 58.

In addition, at the intermediate region 57, the struts 54 are notched or otherwise designed to buckle or bend outwards when compressed. Between the intermediate region 57 of the struts 54 and the distal end 36 of the sheath 32, the guidewire 40 includes a locking member 80, preferably an annular-shaped ring made of stainless steel, fixedly attached thereon. Inside the lumen 33 near the distal end 36, the sheath 32 has a recessed area 82 adapted to receive the locking member 80.

The guidewire 40 and filter assembly 50 are included in a sheath 32 as previously described, which is introduced into a blood vessel 70, as shown in FIG. 4A, downstream of the stenosed region (not shown). With the sheath 32 substantially held in position, the guidewire 40 is pulled proximally. This causes the struts 54 to buckle and fold outward at the intermediate region 57, opening the open end 64 of the filter mesh 60 as shown in FIG. 4B. As the guidewire 40 is pulled, the locking member 80 enters the lumen 33, moving proximally until it engages the recessed area 82, locking the expansion frame in its enlarged condition, as shown in FIG. 4C. With the expansion frame 52 in its enlarged condition, the open end 64 of the filter mesh 60 substantially engages the walls 72 of the blood vessel 70.

After the stent is delivered (not shown), the expansion frame 52 is closed by pushing the guidewire 40 distally. This pulls the struts 54 back in towards the guidewire 40, closing the open end 64 of the filter mesh 60 and holding any loose embolic material within the filter assembly 50.

As a further modification of this embodiment, the entire sheath 32 and filter assembly 50 may be provided within an outer sheath or catheter (not shown) to protect the filter assembly 50 during introduction into the vessel. Once the device is in the desired location, the sheath 32 is held in place and the outer sheath is withdrawn proximally, exposing the filter assembly 50 within the blood vessel 70. After the filter assembly 50 is used and closed, the sheath 32 is pulled proximally until the filter assembly 50 completely enters the outer sheath, which may then be removed.

Figure 5C:
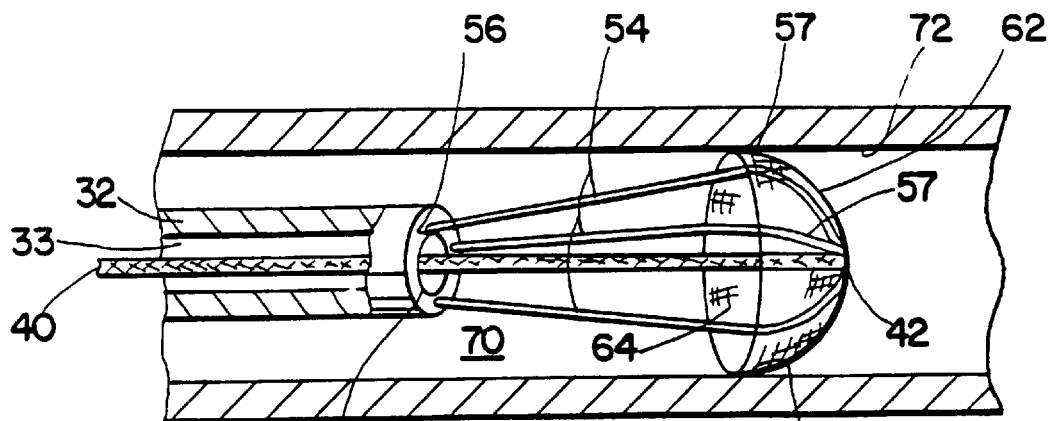
FIGS. 5A, 5B and 5C show a longitudinal view of another embodiment of the filter device in a contracted condition, a partially opened condition, and an enlarged condition across a blood vessel respectively.
Figure 5B:
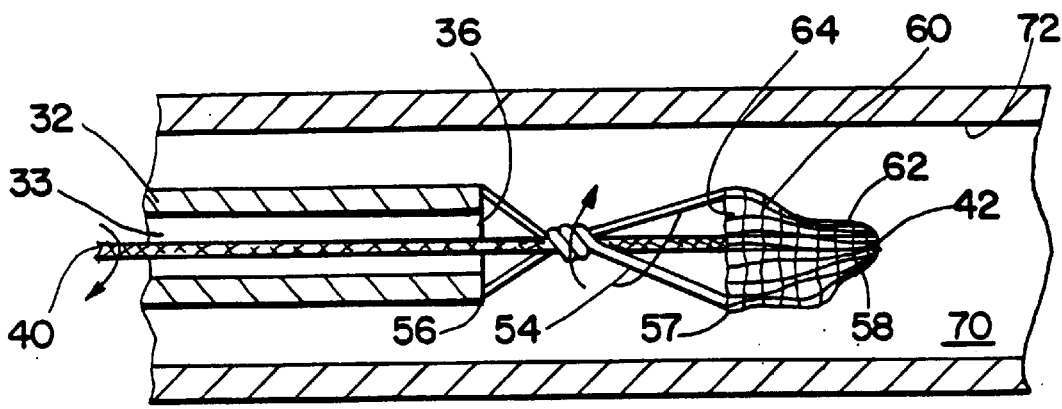
Figure 5A:
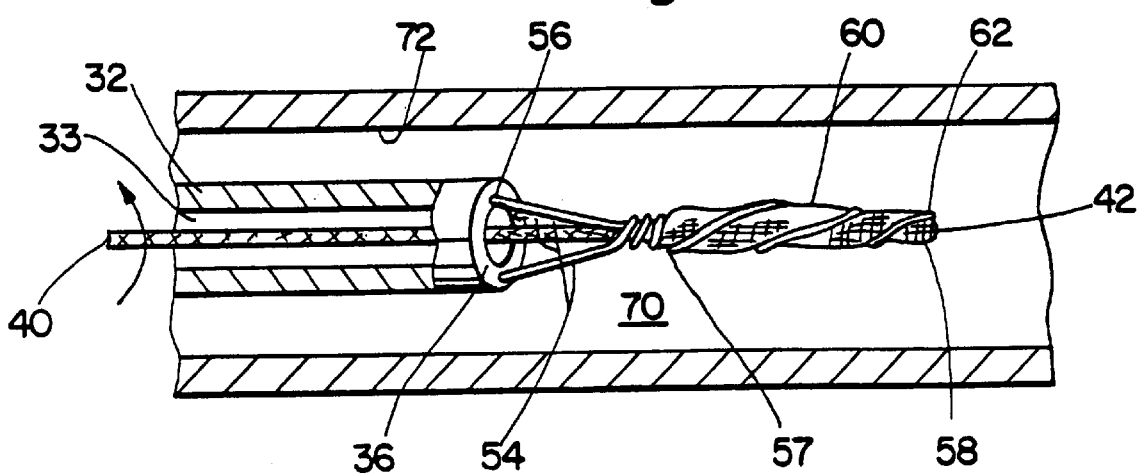

Turning to FIGS. 5A, 5B and 5C, another embodiment of the filter assembly 50 is shown. The proximal ends 56 of the plurality of struts 54 are substantially fixed to the distal end 36 of the sheath 32. The distal ends 58 may terminate at the open end 64 of the filter mesh 60, although preferably, the struts 54 extend distally through the filter mesh 60 to the closed end region 62, where they are attached to the distal end 42 of the guidewire 40.

Referring to FIG. 5A, the filter assembly 50 is shown in its contracted condition. The guidewire 40 has been rotated torsionally, causing the struts 54 to helically twist along the longitudinal axis of the guidewire 40 and close the filter mesh 60. The filter assembly 50 is introduced into a blood vessel 70 as already described, either exposed on the end of the sheath 32 or, preferably, within an outer sheath (not shown) as described above.

Once in position, the sheath 32 is fixed, and the guidewire 40 is rotated torsionally in relation to the sheath 32. As shown in FIG. 5B, the struts 54, which are biased to move radially towards the wall 72 of the vessel 70, unwind as the guidewire 40 is rotated, opening the open end 64 of the filter mesh 60. Once the struts 54 are untwisted, the expansion frame in its enlarged condition causes the open end 64 of the filter mesh 60 to substantially engage the walls 72 of the vessel 70, as shown in FIG. 5C.

After the stent is delivered (not shown), the guidewire 40 is again rotated, twisting the struts 54 back down until the expansion frame 52 again attains the contracted condition of FIG. 5A. The sheath 32 and filter assembly 50 are then removed from the blood vessel 70.

Figure 6A:
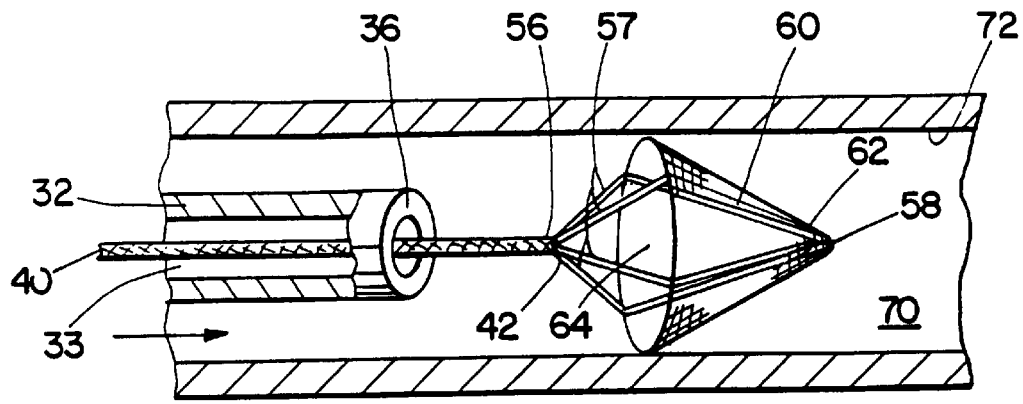
FIGS. 6A and 6B are longitudinal views, showing the orientation of the filter mesh in an antegrade approach to a stenosed region and in a retrograde approach respectively.
Figure 6B:
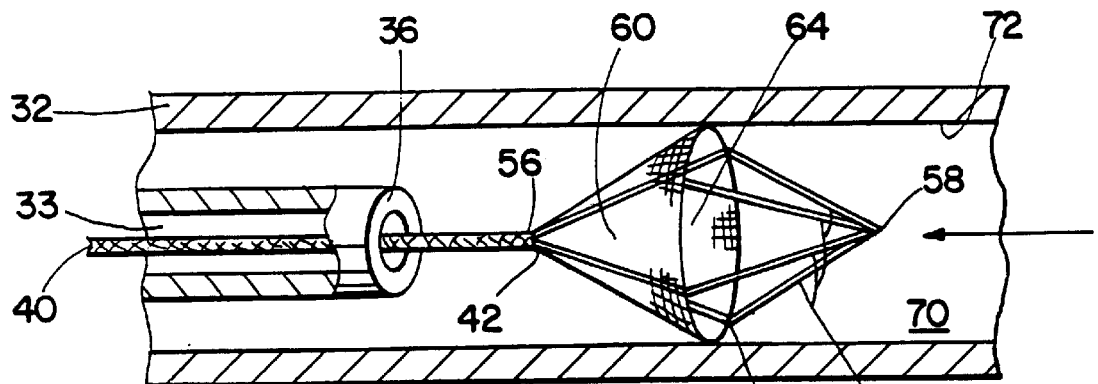

Another embodiment of the filter assembly 50 is shown in FIGS. 6A and 6B. The struts 54 at their proximal ends 56 are mounted on or in contact with guidewire 40, and their distal ends 58 are connected to form the expansion frame 52, and are biased to expand radially at an intermediate region 57. The proximal ends 56 are attached to the distal end 42 of the guidewire 40 with the distal ends 58 being extended distally from sheath 32. Filter mesh 60 is attached to the struts 54 at the intermediate region 57. If the filter assembly 50 is introduced in an antegrade orientation as previously described, the filter mesh 60 is typically attached from the intermediate region 57 to the distal ends 58 of the struts 54, as indicated in FIG. 6A. Alternatively, if introduced in a retrograde orientation, it is preferable to attach the filter mesh 60 between the intermediate region 57 to the proximal ends 56 of the struts 54, as shown in FIG. 6B, thus directing the interior of the filter mesh upstream to capture any embolic material therein.

The filter assembly 50 is provided with the struts 54 compressed radially in a contracted condition in the lumen 33 of the sheath 32 (not shown). The filter assembly 50 is introduced into the blood vessel 70 by directing the guidewire distally. As the expansion frame 52 enters the blood vessel, the struts 54 automatically expand radially into the enlarged condition shown in FIGS. 6A and 6B, thereby substantially engaging the open end 64 of the filter mesh 60 with the walls 72 of the blood vessel 70. To withdraw the filter assembly 50 from the vessel 70, the guidewire 40 is simply pulled proximally. The struts 54 contact the distal end 36 of the sheath 32 as they enter the lumen 33, compressing the expansion frame 52 back into the contracted condition.

Figure 8A:
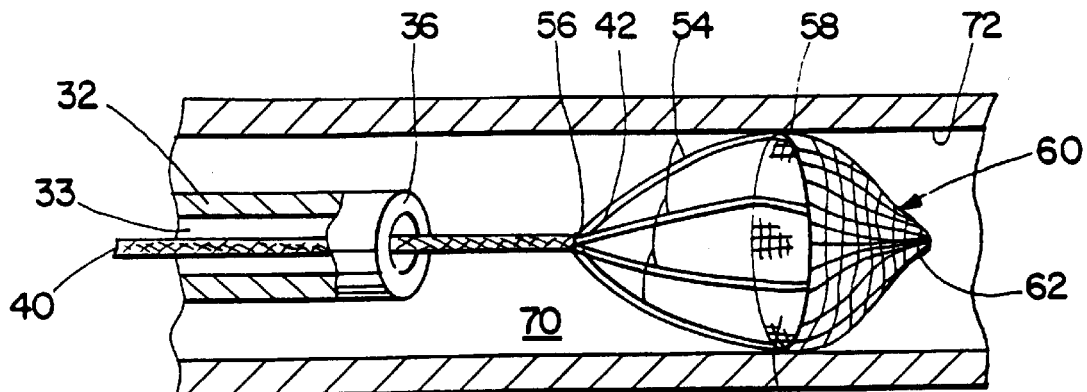
FIGS. 8A and 8B are longitudinal views of another embodiment of the filter assembly, showing the filter mesh without gripping hairs and with gripping hairs respectively.

FIG. 8A presents another embodiment of the filter assembly 50 similar to that just described. The expansion frame 52 comprises a plurality of struts 54 having a filter mesh 60 attached thereon. Rather than substantially straight struts bent at an intermediate region, however, the struts 54 are shown having a radiused shape biased to expand radially when the filter assembly 50 is first introduced into the blood vessel 70. The filter mesh 60 has a substantially hemispherical shape, in lieu of the conical shape previously shown.

Figure 8B:
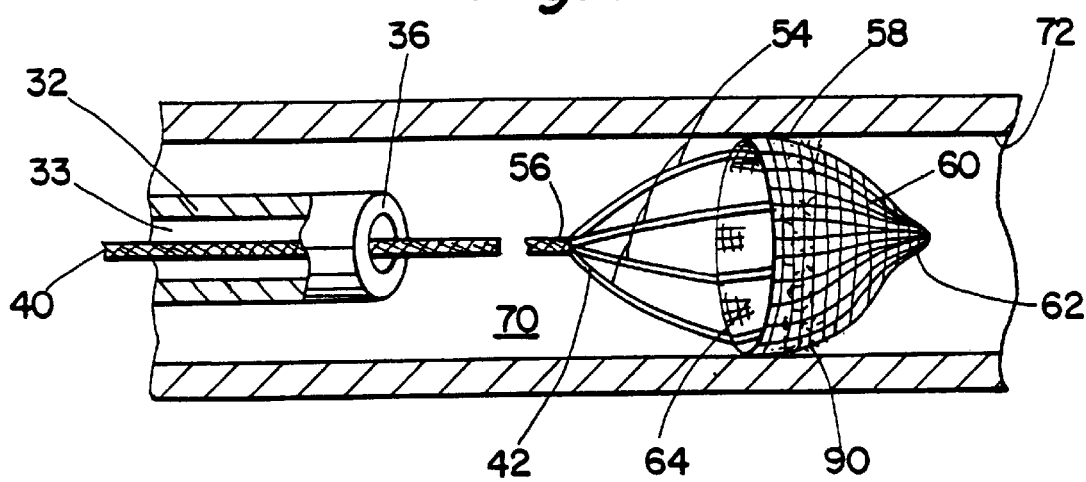

Optionally, as shown in FIG. 8B, the filter mesh 60 may include gripping hairs 90, preferably made from nylon, polyethylene, or polyester, attached around the outside of the open end 64 to substantially minimize undesired movement of the filter mesh 60. Such gripping hairs 90 may be included in any embodiment presented if additional engagement between the filter mesh 60 and the walls 72 of the vessel 70 is desired.

Figure 7:
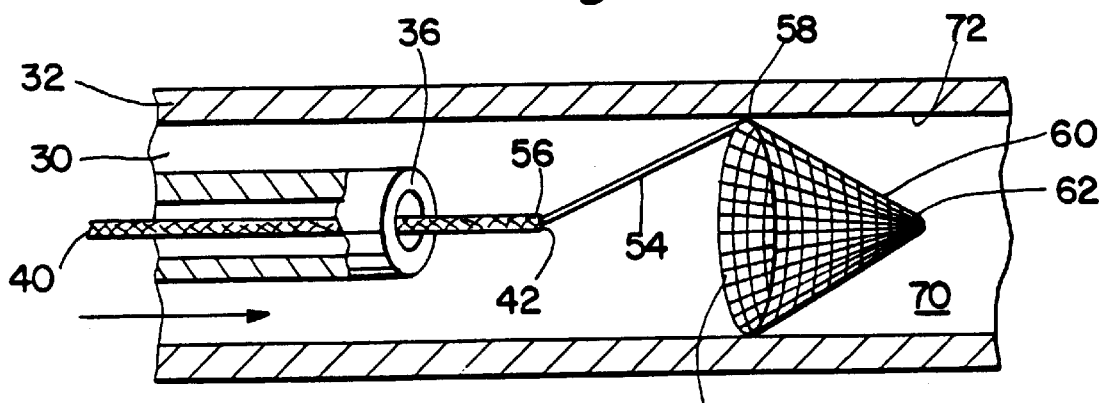
FIG. 7 is a longitudinal view of another embodiment of the filter assembly.

FIG. 7 shows an alternative embodiment of the filter assembly 50, in which the expansion frame 52 comprises a strut 54 attached to the filter mesh 60. The open end 64 of the filter mesh 60 is biased to open fully, thereby substantially engaging the walls 72 of the blood vessel 70. The mesh material itself may provide sufficient bias, or a wire frame (not shown) around the open end 64 may be used to provide the bias to open the filter mesh 60.

The filter mesh 60 is compressed prior to introduction into the sheath 32. To release the filter assembly 50 into the blood vessel 70, the guidewire 40 is moved distally. As the filter assembly 50 leaves the lumen 33 of the sheath 32, the filter mesh 60 opens until the open end 64 substantially engages the walls 72 of the blood vessel 70. The strut 54 attached to the filter mesh 60 retains the filter mesh 60 and eases withdrawal back into the sheath 32. For removal, the guidewire 40 is directed proximally. The strut 54 is drawn into the lumen 33, pulling the filter mesh 60 in after it.

Figure 9:
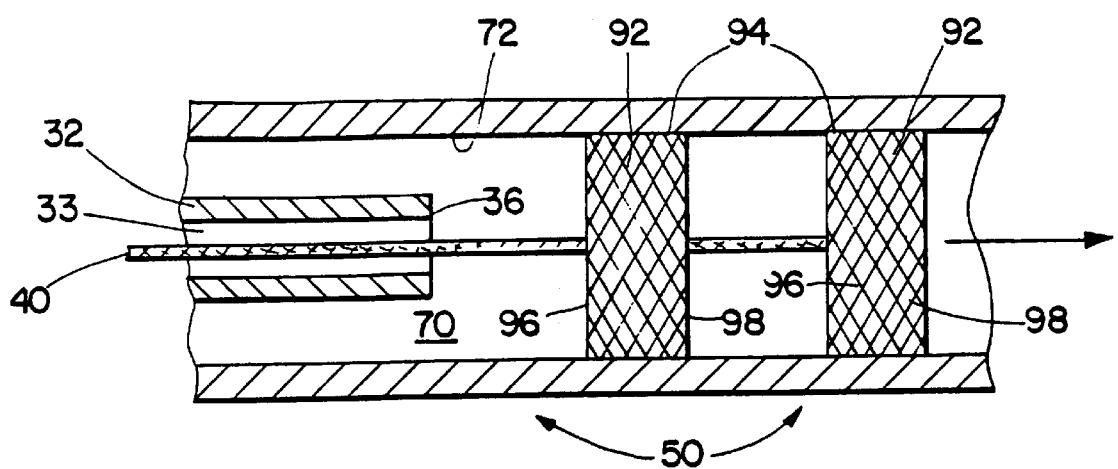
FIG. 9 is a longitudinal view of another embodiment of the filter assembly including sponge-like devices.

In a further alternative embodiment, FIG. 9 shows a filter assembly 50 comprising a plurality of substantially cylindrical, expandable sponge-like devices 92, having peripheral surfaces 94 which substantially engage the walls 72 of the blood vessel 70. The devices 92 are fixed to the guidewire 40 which extends centrally through them as shown. The sponge-like devices have sufficient porosity to allow blood to pass freely through them and yet to entrap undesirable substantially larger particles, such as loose embolic material. Exemplary materials appropriate for this purpose include urethane, silicone, cellulose, or polyethylene, with urethane and polyethylene being preferred.

In addition, the devices 92 may have varying porosity, decreasing along the longitudinal axis of the guidewire. The upstream region 96 may allow larger particles, such as embolic material, to enter therein, while the downstream region 98 has sufficient density to capture and contain such material. This substantially decreases the likelihood that material will be caught only on the outer surface of the devices, and possibly come loose when the devices is drawn back into the sheath.

The devices 92 are compressed into the lumen 33 of the sheath 32 (not shown), defining the contracted condition. They are introduced into the blood vessel 70 by pushing the guidewire 40 distally. The devices 92 enter the vessel 70 and expand substantially into their uncompressed size, engaging the walls 72 of the vessel 70. After use, the guidewire 40 is pulled proximally, compressing the devices 92 against the distal end 36 of the sheath 32 and directing them back into the lumen 33.

Figure 10:
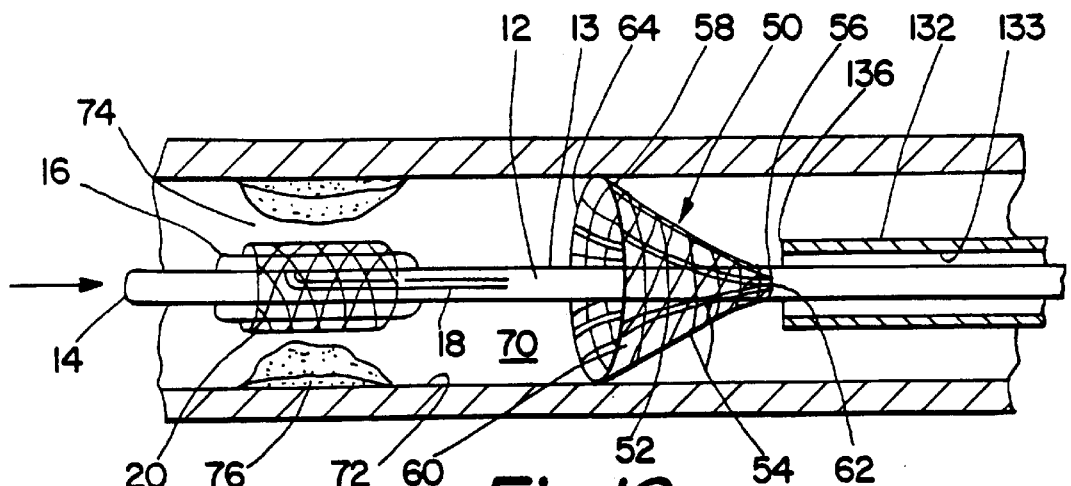
FIG. 10 is a longitudinal view of another embodiment, namely a filter assembly attached to the outer surface of a stent catheter.

Turning to FIG. 10, another embodiment of the present invention is shown, that is, a stent catheter 10 having a filter assembly 50 provided directly on its outer surface 13. The stent catheter 10 includes similar elements and materials to those already described, namely a catheter 12, an inflatable balloon 16 near the distal end 14 of the catheter 12, and a stent 20 compressed over the balloon 16. Instead of providing a filter assembly 50 on a guidewire, however, the filter assembly 50 typically comprises an expansion frame 52 and filter mesh 60 attached directly to the outer surface 13 of the catheter 12. Preferably, the expansion frame 52 is attached to the catheter 12 in a location proximal of the stent 20 for use in retrograde orientations, although optionally, the expansion frame 52 may be attached distal of the stent 20 and used for antegrade applications.

The filter assembly 50 may take many forms similar to those previously described for attachment to a guidewire. In FIG. 10, the expansion frame 52 includes a plurality of radially biased struts 54, having proximal ends 56 and distal ends 58. The proximal ends 56 of the struts 54 are attached to the outer surface 13 of the catheter 12 proximal of the stent 20, while the distal ends 58 are loose. Filter mesh 60, similar to that already described, is attached to the struts 54 between the proximal ends 56 and the distal ends 58, and optionally to the outer surface 13 of the catheter 12 where the proximal ends 56 of the struts 52 are attached.

Prior to use, a sheath 132 is generally directed over the catheter 12. When the sheath engages the struts 54, it compresses them against the outer surface 13 of the catheter 12. The catheter 12 and the sheath 132 are then introduced into the patient, and directed to the desired location. Once the stent 20 is in position, the catheter 12 is fixed and the sheath 132 is drawn proximally. As the struts 58 enter the blood vessel 70, the distal ends 58 move radially, opening the filter mesh 60. Once the filter assembly 50 is fully exposed within the blood vessel 70, the distal ends 58 of the struts 54, and consequently the open end 64 of the filter mesh 60, substantially engage the walls 72 of the blood vessel 70.

After the stent is deployed, the sheath 132 is pushed distally. As the struts 54 enter the lumen 133 of the sheath 132, they are compressed back against the outer surface 13 of the catheter 12, thereby containing any captured material in the filter mesh 60. The catheter 12 and sheath 132 are then withdrawn from the vessel 70.

Figure 11A:
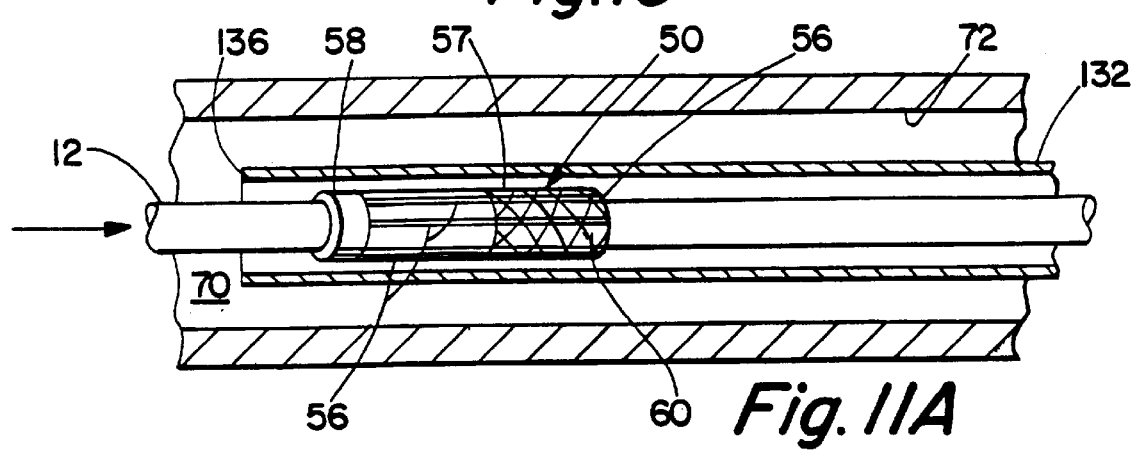
FIGS. 11A and 11B show a filter assembly attached to the outer surface of a stent catheter, with a sheath retaining the filter assembly in the contracted condition, and with the filter assembly in the enlarged condition respectively.
Figure 11B:
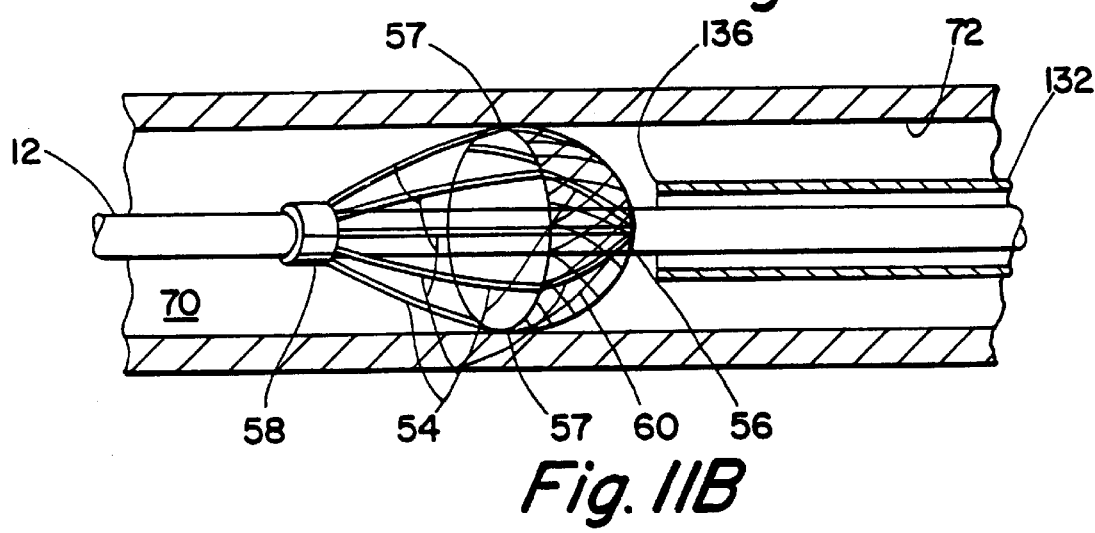

Turning to FIGS. 11A and 11B, an alternative embodiment of the expansion frame 50 is shown. The proximal ends 56 of the struts 54 are attached or in contact with the outer surface 13 of the catheter 12. The struts 54 have a contoured radius biased to direct an intermediate region 57 radially. Filter mesh 60 is attached between the intermediate region 57 and the proximal ends 56, or between the intermediate region and the distal end (not shown). FIG. 11A shows the filter assembly 50 in its contracted condition, with a sheath 132 covering it. The sheath 132 compresses the struts 54 against the outer surface 13 of the catheter 12, allowing the device to be safely introduced into the patient. Once in position, the sheath 132 is pulled proximally as shown in FIG. 11B. As the distal end 136 of the sheath 132 passes proximal of the filter assembly 50, the struts 54 move radially, causing the intermediate region 57 of the struts 54 and the open end of the filter mesh 60 to substantially engage the walls 72 of the blood vessel 70. After use, the sheath 132 is directed distally, forcing the struts 54 back against the catheter 12 and containing any material captured within the filter mesh 60.

Figure 12A:
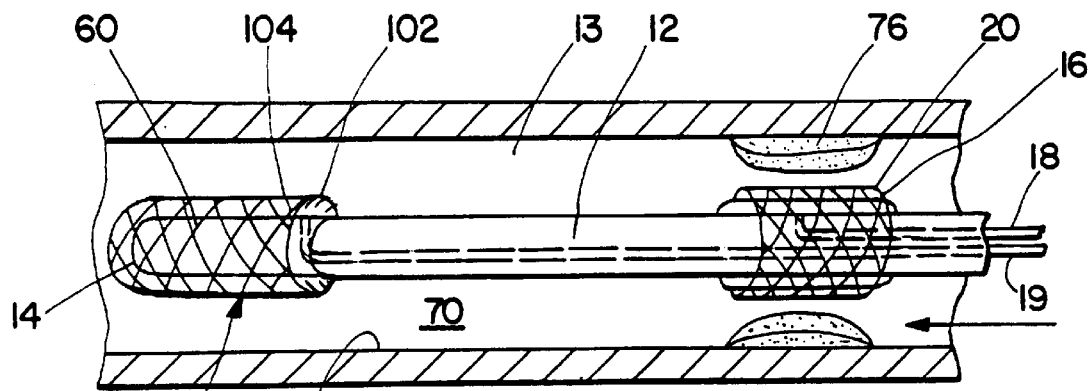
FIGS. 12A and 12B are longitudinal views of another embodiment including an inflatable filter assembly, shown in a contracted condition and an enlarged condition respectively.
Figure 12B:
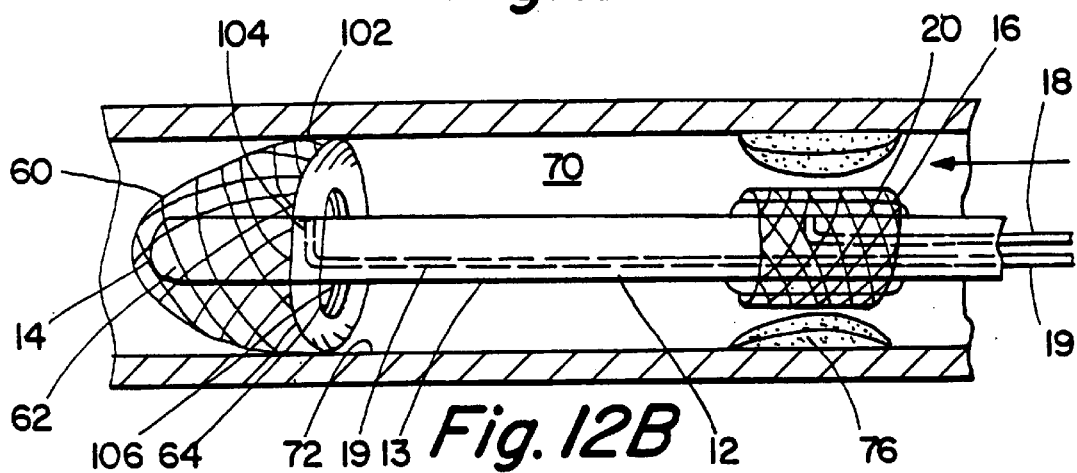

In another embodiment of the present invention, shown in FIGS. 12A and 12B, a stent catheter 10, similar to those previously described, is provided with a fluid operated filter assembly 50 attached on or near the distal end 14 of the catheter 12. The catheter 12 includes a first inflation lumen 18 for the stent balloon 16, and a second inflation lumen 19 for inflating an expansion frame 52 for the filter assembly 50. The expansion frame 52 generally comprises an inflatable balloon 102, preferably having a substantially annular shape. The balloon 102 generally comprises a flexible, substantially resilient material, such as silicone, latex, or urethane, but with urethane being preferred.

The second inflation lumen 19 extends to a region at or near to the distal end 14 of the catheter 12, and then communicates with the outer surface 13, or extends completely to the distal end 14. A conduit 104 extends between the balloon 102 and the inflation lumen 19. The conduit 104 may comprise a substantially flexible tube of material similar to the balloon 102, or alternatively it may be a substantially rigid tube of materials such as polyethylene. Optionally, struts or wires 106 are attached between the balloon 102 and the catheter 12 to retain the balloon 12 in a desired orientation. Filter mesh 60, similar to that previously described, is attached to the balloon 102.

Turning more particularly to FIG. 12A, the filter assembly 50 is shown in its contracted condition. The balloon 102 is adapted such that in its deflated condition it substantially engages the outer surface 13 of the catheter 12. This retains the filter mesh 60 against the catheter 12, allowing the catheter 12 to be introduced to the desired location within the patient's blood vessel 70. The catheter 12 is percutaneously introduced into the patient and the stent 20 is positioned within the occluded region 74. Fluid, such as saline solution, is introduced into the lumen 19, inflating the balloon 102. As it inflates, the balloon 102 expands radially and moves away from the outer surface 13 of the catheter 12.

As shown in FIG. 12B, once the balloon 102 is fully inflated to its enlarged condition, it substantially engages the walls 72 of the blood vessel 70 and opens the filter mesh 60. Once the stent 20 is delivered and the stent balloon 16 is deflated, fluid is drawn back out through the inflation lumen 19, deflating the balloon 102. Once deflated, the balloon 102 once again engages the outer surface 13 of the catheter 12, closing the filter mesh 60 and containing any embolic material captured therein. The catheter 12 is then withdrawn from the patient.

Figure 13:
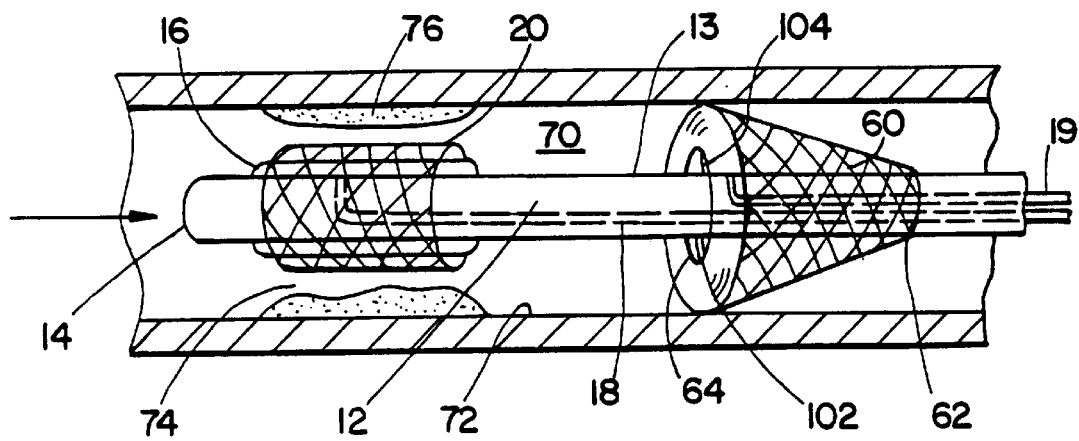
FIG. 13 is a longitudinal view of an inflatable filter assembly attached to the catheter proximal of the stent shown in an enlarged condition.

Alternatively, the filter assembly 50 just described may be mounted in a location proximal to the stent 20 as shown in FIGS. 13A and 13B. The open end 64 of the filter mesh 60 is attached to the balloon 102, while the closed end 62 is attached to the outer surface 13 of the catheter 12, thereby defining a space for capturing embolic material. In the contracted condition shown in FIG. 13A, the balloon 102 substantially engages the outer surface 13 of the catheter 12, thereby allowing the catheter 10 to be introduced or withdrawn from a blood vessel 70. Once the stent 20 is in position across a stenosed region 74, the balloon 102 is inflated, moving it away from the catheter 12, until it achieves its enlarged condition, shown in FIG. 13B, whereupon it substantially engages the walls 72 of the blood vessel 70.

Figure 15:
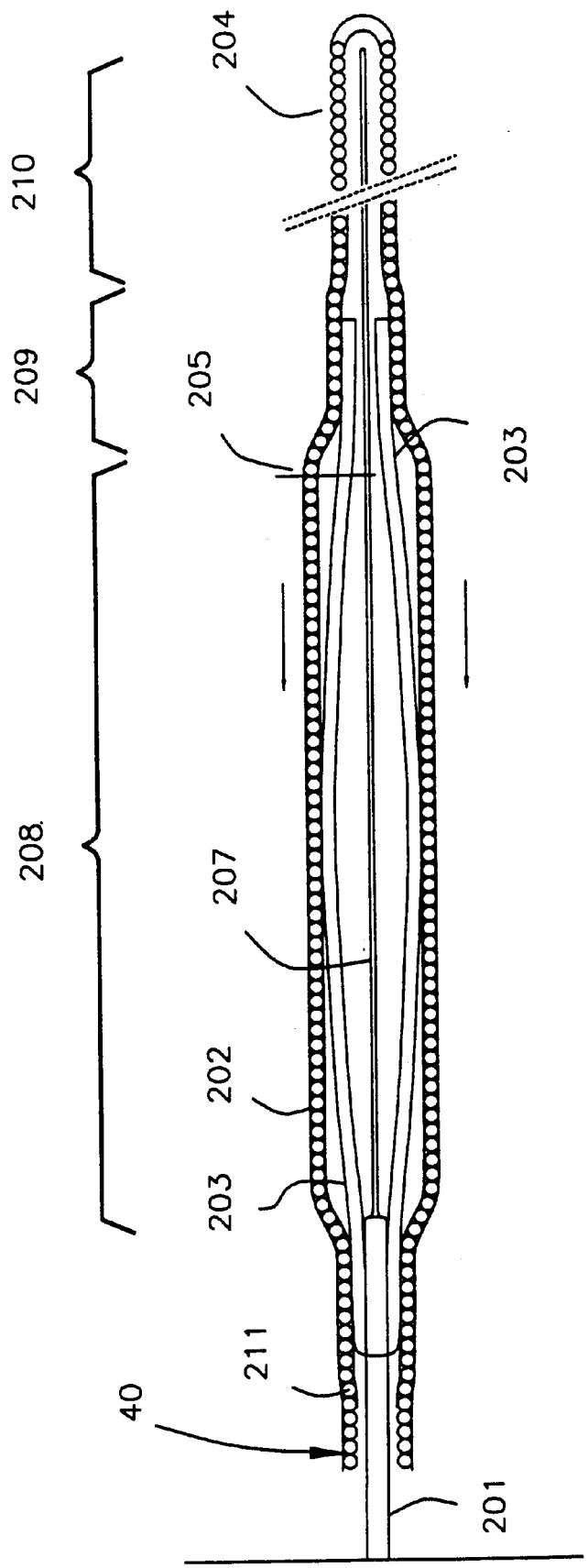

A detailed longitudinal view of a filter guidewire is shown in FIG. 15. Guidewire 40 comprises inner elongate member 207 surrounded by a second elongate member 201, about which is wrapped wire 211 in a helical arrangement. Guidewire 40 includes enlarged segment 202, 208 which houses a series of radially biased struts 203. Helical wires 211 separate at cross-section 205 to expose the eggbeater filter contained within segment 202. Guidewire 40 includes a floppy atramatic tip 204 which is designed to navigate through narrow, restricted vessel lesions. The eggbeater filter is deployed by advancing distally elongate member 201 so that wire housing 211 separates at position 205 as depicted in FIG. 15A. Elongate member 207 may be formed from a longitudinally stretchable material which compresses as the struts 203 expand radially. Alternatively, elongate member 207 may be slidably received within sheath 201 to allow radial expansion of struts 203 upon deployment. The filter guidewire may optionally include a coil spring 206 disposed helically about elongate member 207 in order to cause radial expansion of struts 203 upon deployment.

A typical filter guidewire will be constructed so that the guidewire is about 5F throughout segment 208, 4F throughout segment 209, and 3F throughout segment 210. The typical outer diameter in a proximal region will be 0.012–0.035 inches, more preferably 0.016–0.022 inches, more preferably 0.018 inches. In the distal region, a typical outer diameter is 0.020–0.066 inches, more preferably 0.028–0.036 inches, more preferably 0.035 inches. Guidewire length will typically be 230–290 cm, more preferably 260 cm for deployment of a balloon catheter. It should be understood that reducing the dimensions of a percutaneous medical instrument to the dimensions of a guidewire as described above is a significant technical hurdle, especially when the guidewire includes a functioning instrument such as an expansible filter as disclosed herein. It should also be understood that the above parameters are set forth only to illustrate typical device dimensions, and should not be considered limiting on the subject matter disclosed herein.

In use, a filter guidewire is positioned in a vessel at a region of interest. The filter is deployed to an expanded state, and a medical instrument such as a catheter is advanced over the guidewire to the region of interest. Angioplasty, stent deployment, rotoblader, atherectomy, or imaging by ultrasound or Doppler is then performed at the region of interest. The medical/interventional instrument is then removed from the patient. Finally, the filter is compressed and the guidewire removed from the vessel.

Figure 16:
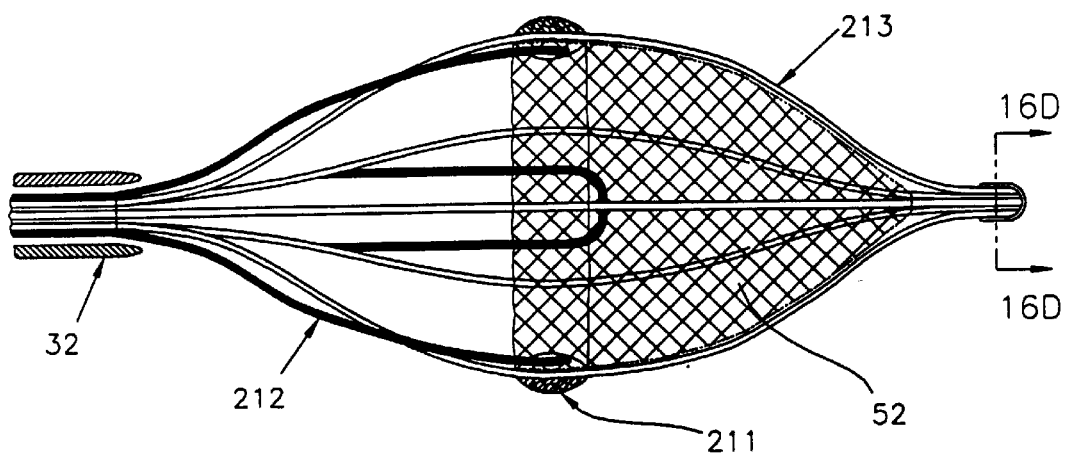
FIGS. 16, 16A, 16B, and 16C show longitudinal and cross-sectional views of an eggbeater filter in accordance with the present invention.
Figure 16D:
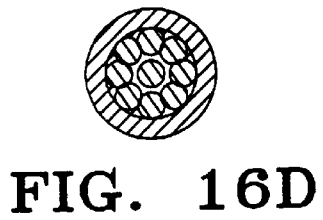
Figure 16A:
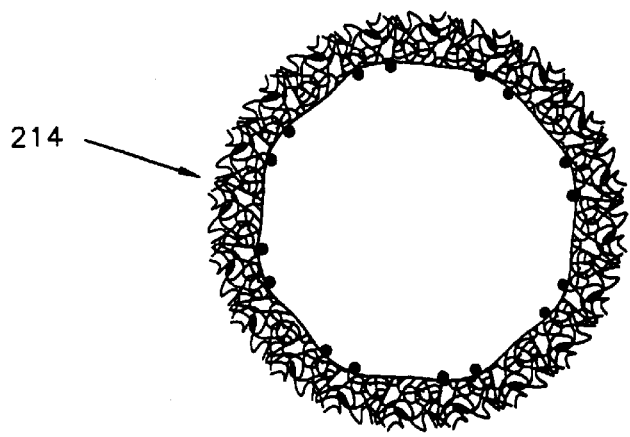
Figure 16B:
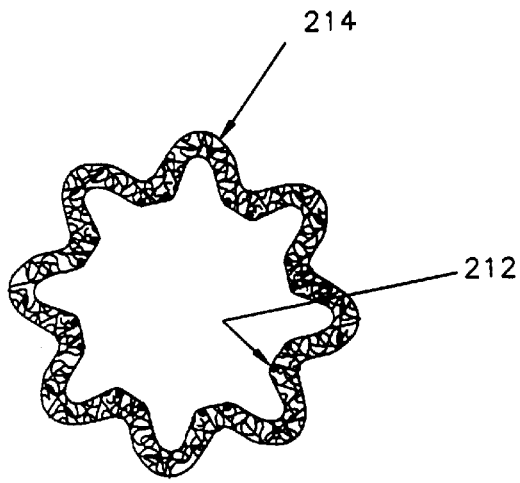
Figure 16C:
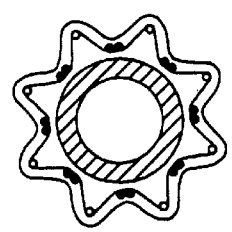

A detailed depiction of an eggbeater filter is shown in FIGS. 16, 16A, 16B, and 16C. With reference to FIG. 16, the eggbeater filter includes pressure wires 212, primary wire cage 213, mesh 52, and optionally a foam seal 211 which facilitates substantial engagement of the interior lumen of a vessel wall and conforms to topographic irregularities therein. The eggbeater filter is housed within catheter sheath 32 and is deployed when the filter is advanced distally beyond the tip of sheath 32. This design will accommodate a catheter of size 8F (0.062 inches, 2.7 mm), and for such design, the primary wire cage 213 would be 0.010 inches and pressure wires 212 would be 0.008 inches. These parameters can be varied as known in the art, and therefore should not be viewed as limiting. FIGS. 16A and 16B depict the initial closing sequence at a cross-section through foam seal 214. FIG. 16C depicts the final closing sequence.

FIGS. 17 and 17A depict an alternative filter guidewire which makes use of a filter scroll 215 disposed at the distal end of guidewire 40. Guidewire 40 is torsionally operated as depicted at 216 in order to close the filter, while reverse operation (217) opens the filter. The filter scroll may be biased to automatically spring open through action of a helical or other spring, or heat setting. Alternatively, manual, torsional operation opens the filter scroll. In this design, guidewire 40 acts as a mandrel to operate the scroll 215.

Figure 18:
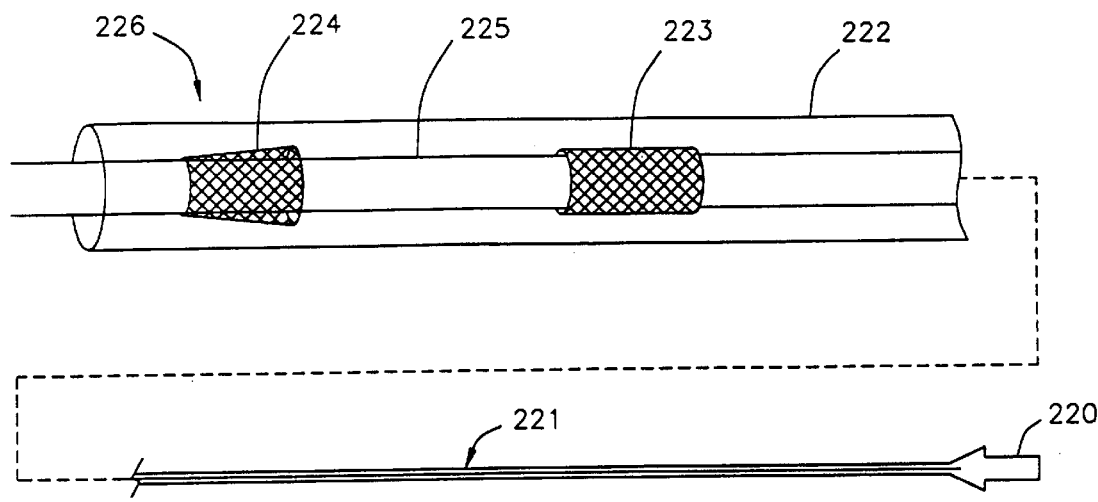
FIGS. 18, 18A, and 18B show longitudinal views of a filter catheter in accordance with the present invention.
Figure 18A:
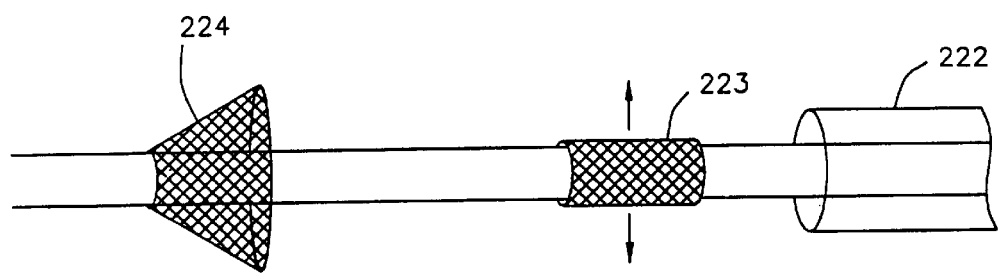
Figure 18B:
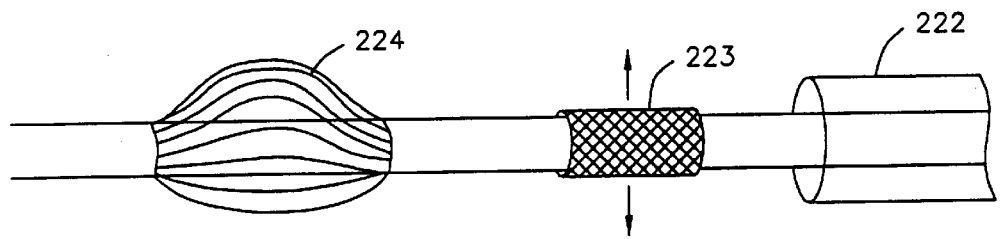

An alternative embodiment of a stent deployment blood filtration device is depicted in FIGS. 18, 18A, and 18B. With reference to FIG. 18, catheter 225 includes housing 220 at its proximal end 221, and at its distal end catheter 225 carries stent 223 and expandable filter 224. In one embodiment, expandable filter 224 is a self-expanding filter device optionally disposed about an expansion frame. In another embodiment, filter 224 is manually operable by controls at proximal region 221 for deployment. Similarly, stent 223 can be either a self-expanding stent as discussed above, or a stent which is deployed using a balloon or other radially expanding member. Restraining sheath 222 encloses one or both of filter 224 and stent 223. In use, distal region 226 of catheter 225 is disposed within a region of interest, and sheath 222 is drawn proximally to first exposed filter 224 and then exposed stent 223. As such, filter 224 deploys before stent 223 is radially expanded, and therefore filter 224 is operably in place to capture any debris dislodged during stent deployment as depicted in FIG. 18A. FIG. 18B shows an alternative embodiment which employs eggbeater filter 224 in the distal region.

Figure 19:
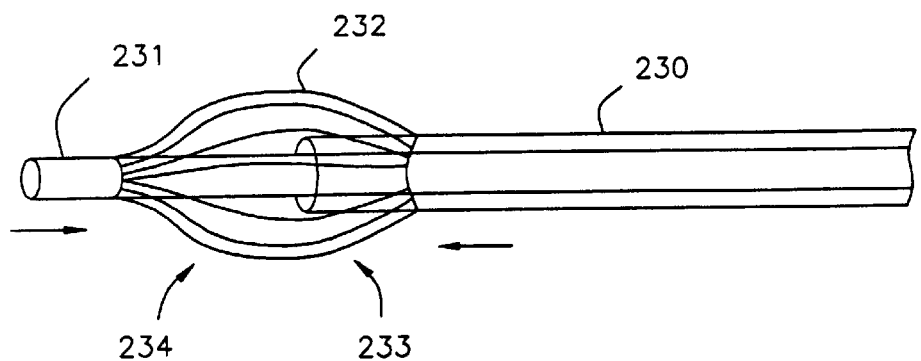
FIG. 19 shows an alternate construction for an eggbeater filter as disclosed herein.

An alternative design for the construction of an eggbeater filter is shown in FIG. 19. This device includes inner sheath 231, outer sheath 230, and a plurality of struts 232 which are connected to outer sheath 230 at a proximal end of each strut, and to inner sheath 231 at a distal end of each strut. Filter expansion is accomplished by moving inner sheath 231 proximal relative to outer sheath 230, which action causes each strut to buckle outwardly. It will be understood that the struts in an eggbeater filter may be packed densely to accomplish blood filtration without a mesh, or may include a mesh draped over a proximal portion 233 or a distal portion 234, or both.

Figure 20:
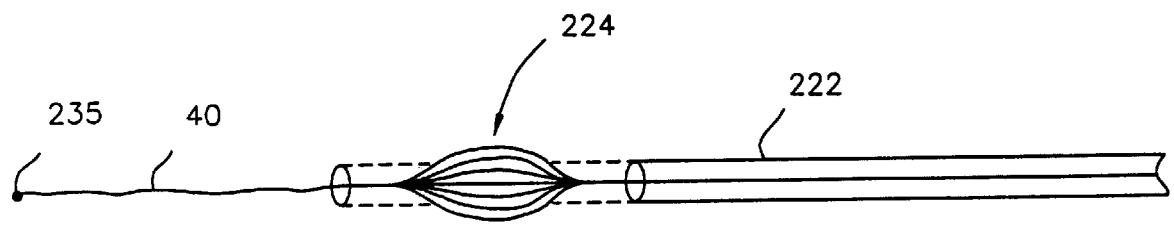
FIG. 20 shows a longitudinal view of an imaging guidewire having an eggbeater filter and restraining sheath.

In another embodiment, a filter guidewire is equipped with a distal imaging device as shown in FIG. 20. Guidewire 40 includes eggbeater filter 224 and restraining sheath 222 for deployment of filter 224. The distal end of guidewire 40 is equipped with imaging device 235 which can be any of an ultrasound transducer or a Doppler flow velocity meter, both capable of measuring blood velocity at or near the end of the guidewire. Such a device provides valuable information for assessment of relative blood flow before and after stent deployment. Thus, this device will permit the physician to determine whether the stent has accomplished its purpose or been adequately expanded by measuring and comparing blood flow before and after stent deployment.

In use, the distal end of the guidewire is introduced into the patient's vessel with the sheath covering the expandable filter. The distal end of the guidewire is positioned so that the filter is downstream of a region of interest and the sheath and guidewire cross the region of interest. The sheath is slid toward the proximal end of the guidewire and removed from the vessel. The expandable filter is uncovered and deployed within the vessel downstream of the region of interest. A percutaneous medical instrument is advanced over the guidewire to the region of interest and a procedure is performed on a lesion in the region of interest. The percutaneous medical instrument can be any surgical tool such as devices for stent delivery, balloon angioplasty catheters, atherectomy catheters, a rotoblader, an ultrasound imaging catheter, a rapid exchange catheter, an over-the-wire catheter, a laser ablation catheter, an ultrasound ablation catheter, and the like. Embolic material generated during use of any of these devices on the lesion is captured before the expandable filter is removed from the patient's vessel. The percutaneous instrument is then withdrawn from the vessel over the guidewire. A sheath is introduced into the vessel over the guidewire and advanced until the sheath covers the expandable filter. The guidewire and sheath are then removed from the vessel.

Figure 21:
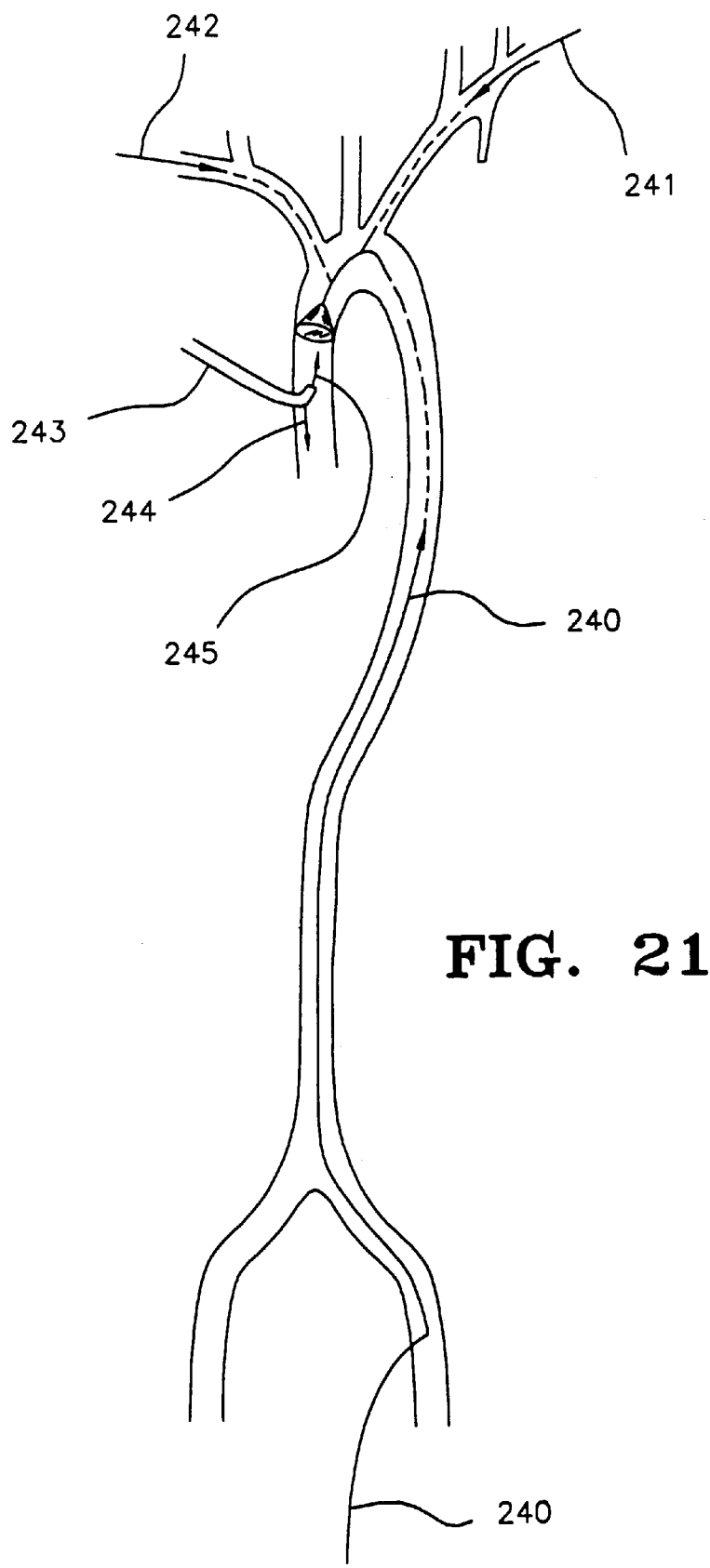
FIG. 21 shows human aortic anatomy and depicts several routes for deployment of an aortic filter upstream of the carotid arteries.

Human aortic anatomy is depicted in FIG. 21. During cardiac surgery, bypass cannula 243 is inserted in the ascending aorta and either balloon occlusion or an aortic cross-clamp is installed upstream of the entry point for cannula 243. The steps in a cardiac procedure are described in Barbut et al., U.S. application Ser. No. [Lyon & Lyon attorney docket no. 224/194], filed Apr. 16, 1997, and the level of debris dislodgement is described in Barbut et al., "Cerebral Emboli Detected During Bypass Surgery Are Associated With Clamp Removal," Stroke, 25(12):2398–2402 (1994), which is incorporated herein by reference in its entirety. FIG. 21 demonstrates that the decoupling of the filter from the bypass cannula presents several avenues for filter deployment. As discussed in Maahs, U.S. application Ser. No. [Lyon & Lyon attorney docket no. 225/108], filed May 8, 1997, and incorporated herein by reference, a modular filter may be deployed through cannula 243 either upstream 244 or downstream 245. In accordance with the present disclosure, a filter may be deployed upstream of the innominate artery within the aorta by using a filter guidewire which is inserted at 240 through a femoral artery approach. Alternatively, filter guidewire may be inserted through route 241 by entry into the left subclavian artery or by route 242 by entry through the right subclavian artery, both of which are accessible through the arms. The filter guidewire disclosed herein permits these and any other routes for accessing the ascending aorta and aortic arch for blood filtration.

Figure 22:
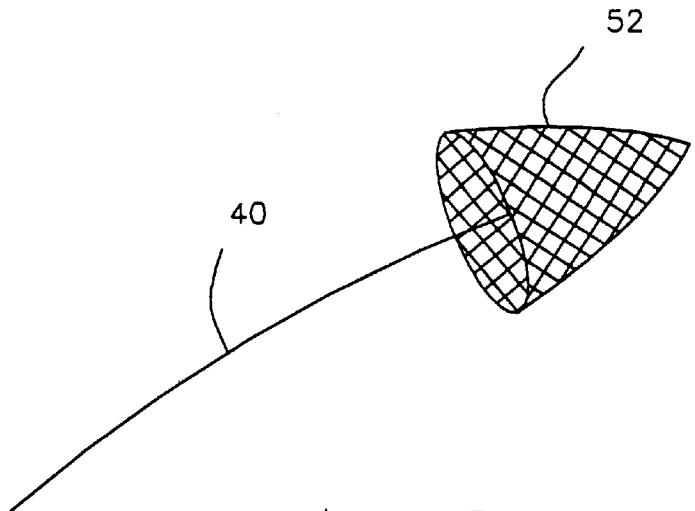
FIG. 22 depicts a longitudinal view of a generalized filter guidewire.
Figure 23:
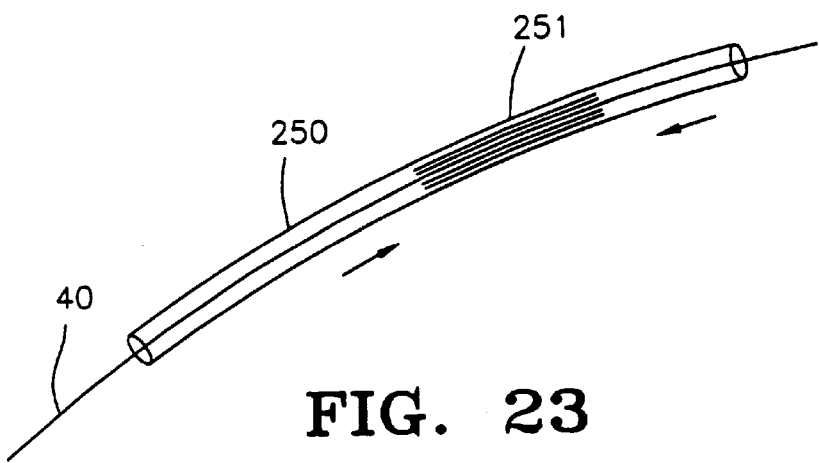
FIGS. 23 and 23A depict longitudinal views of a compressible, expansible sheath disposed over a guidewire in accordance with the present disclosure.
Figure 23A:
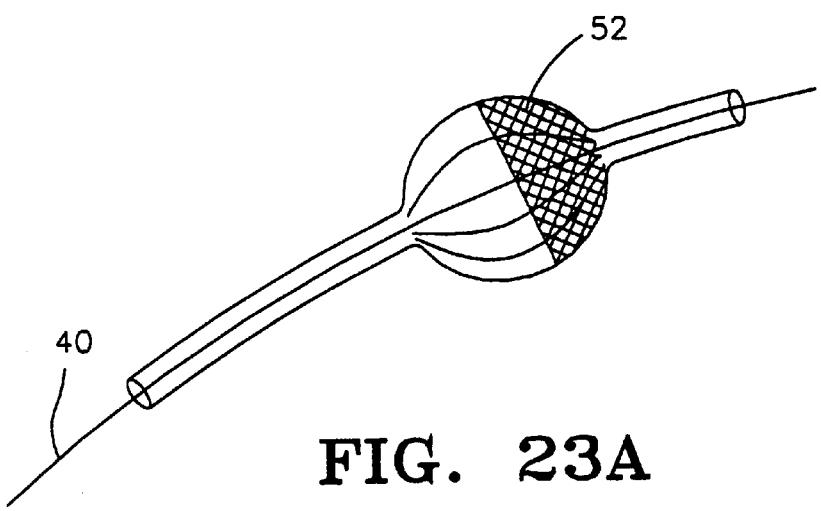

In another embodiment, a generalized filter guidewire is depicted in FIG. 22. FIG. 23 shows guidewire 40 having sleeve 250 disposed thereabout. Sleeve 250 includes longitudinally slitted region 251 which is designed to radially expand when compressed longitudinally. Thus, when the distal end of sleeve 250 is pulled proximally, the slitted region 251 buckles radially outwardly as shown in FIG. 23A to provide a form of eggbeater filter. The expanded cage thus formed may optionally include mesh 52 draped over a distal portion, a proximal portion, or both.

In use, a stent catheter, such as those previously described, is used in a retrograde application, preferably to prevent the detachment of mobile aortic plaque deposits within the ascending aorta, the aortic arch, or the descending aorta. Preferably, the stent catheter is provided with a filter assembly, such as that just described, attached to the catheter proximal of the stent. Alternatively, a stent catheter without any filter device, may also be used. The stent catheter is percutaneously introduced into the patient and directed to the desired region. Preferably, the catheter is inserted into a femoral artery and directed into the aorta, or is introduced into a carotid artery and directed down into the aorta. The stent is centered across the region which includes one or more mobile aortic deposits.

If a filter assembly is provided on the catheter, it is expanded to its enlarged condition before the stent is deployed in order to ensure that any material inadvertently dislodged is captured by the filter. Alternatively, a sheath having a guidewire and filter assembly similar to those previously described may be separately percutaneously introduced downstream of the region being treated, and opened to its enlarged condition.

The stent balloon is inflated, expanding the stent to engage the deposits. The stent forces the deposits against the wall of the aorta, trapping them. When the balloon is deflated, the stent substantially maintains its inflated cross-section, substantially permanently containing the deposits and forming a portion of the lumen of the vessel. Alternatively, a self-expanding stent may be delivered, using a sheath over the stent catheter as previously described. Once the stent has been deployed, the filter assembly is closed, and the stent catheter is withdrawn using conventional methods.

Unlike the earlier embodiments described, this method of entrapping aortic plaque is for a purpose other than to increase luminal diameter. That is, mobile aortic deposits are being substantially permanently contained beneath the stent to protect a patient from the risk of embolization caused by later detachment of plaque. Of particular concern are the ascending aorta and the aortic arch. Loose embolic material in these vessels presents a serious risk of entering the carotid arteries and traveling to the brain, causing serious health problems or possibly even death. Permanently deploying a stent into such regions substantially reduces the likelihood of embolic material subsequently coming loose within a patient, and allows treatment without expensive intrusive surgery to remove the plaque.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method of protecting a patient from embolization during cardiac surgery, comprising the steps of:

providing a blood filter device having a filter disposed on a distal region of an elongate member, the filter adapted to operate at a site within the aorta of the patient and to be removed thereafter;

introducing the blood filter device into the femoral artery and advancing the distal region of the elongate member to the site within the aorta upstream of the innominate artery;

deploying the filter at the site within the aorta;

manipulating the aorta in a region upstream of the site within the aorta; and removing the blood filter device from the aorta, wherein embolic material is generated and filtered before the blood filter device is removed from the aorta.

2. The method of claim 1, further comprising the steps of introducing a blood bypass cannula into the aorta.

3. The method of claim 2, wherein the cannula is introduced downstream of the site where the filter is deployed.

4. The method of claim 1, wherein the step of manipulating the aorta comprises blocking the aorta.

5. The method of claim 4, wherein the step of blocking the aorta includes cross-clamping the aorta.

6. The method of claim 1, wherein the step of manipulating the aorta comprises unblocking the aorta while the blood filter device is deployed within the aorta.

7. The method of claim 1, wherein said elongate member is a catheter.

8. The method of claim 1, wherein said elongate member is a guidewire.

9. A method of protecting a patient from embolization during cardiac surgery, comprising the steps of:

providing a blood filter device having a filter disposed on a distal region of an elongate member, the filter adapted to operate at a site within the aorta of the patient and to be removed thereafter;

introducing the blood filter device into the left subclavian artery and advancing the distal region of the elongate member to the site within the aorta upstream of the innominate artery;

deploying the filter at the site within the aorta;

manipulating the aorta in a region upstream of the site within the aorta; and removing the blood filter device from the aorta, wherein embolic material is generated and filtered before the blood filter device is removed from the aorta.

10. The method of claim 9, further comprising the steps of introducing a blood bypass cannula into the aorta.

11. The method of claim 10, wherein the cannula is introduced downstream of the site where the filter is deployed.

12. The method of claim 9, wherein the step of manipulating the aorta comprises blocking the aorta.

13. The method of claim 12, wherein the step of blocking the aorta includes cross-clamping the aorta.

14. The method of claim 9, wherein the step of manipulating the aorta comprises unblocking the aorta while the blood filter device is deployed within the aorta.

15. The method of claim 9, wherein said elongate member is a catheter.

16. The method of claim 9, wherein said elongate member is a guidewire.

17. A method of protecting a patient from embolization during cardiac surgery, comprising the steps of:

providing a blood filter device having a filter disposed on a distal region of an elongate member, the filter adapted to operate at a site within the aorta of the patient and to be removed thereafter;

introducing the blood filter device into the right subclavian artery and advancing the distal region of the elongate member to the site within the aorta upstream of the innominate artery;

deploying the filter at the site within the aorta;

manipulating the aorta in a region upstream of the site within the aorta; and removing the blood filter device from the aorta, wherein embolic material is generated and filtered before the blood filter device is removed from the aorta.

18. The method of claim 17, further comprising the steps of introducing a blood bypass cannula into the aorta.

19. The method of claim 18, wherein the cannula is introduced downstream of the site where the filter is deployed.

20. The method of claim 17, wherein the step of manipulating the aorta comprises blocking the aorta.

21. The method of claim 20, wherein the step of blocking the aorta includes cross-clamping the aorta.

22. The method of claim 17, wherein the step of manipulating the aorta includes unblocking the aorta while the blood filter device is deployed within the aorta.

23. The method of claim 17, wherein said elongate member is a catheter.

24. The method of claim 17, wherein said elongate member is a guidewire.

25. The catheter of claim 17, wherein the expansion frame is activated by inflating an annular balloon at the base of the struts.

* * * * *